United States Patent
Bae et al.

(10) Patent No.: US 10,047,067 B2
(45) Date of Patent: Aug. 14, 2018

(54) COMPOSITION FOR TREATING KIDNEY DISEASE COMPRISING PYRAZOLE DERIVATIVE

(71) Applicant: Ewha University-Industry Collaboration Foundation, Seoul (KR)

(72) Inventors: Yun Soo Bae, Goyang-si (KR); Hun Joo Ha, Seoul (KR); Kee In Lee, Daejeon (KR); Kyung Hee Song, Seoul (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 168 days.

(21) Appl. No.: 14/424,771

(22) PCT Filed: Aug. 2, 2013

(86) PCT No.: PCT/KR2013/006985
§ 371 (c)(1),
(2) Date: Feb. 27, 2015

(87) PCT Pub. No.: WO2014/035070
PCT Pub. Date: Mar. 6, 2014

(65) Prior Publication Data
US 2015/0218125 A1    Aug. 6, 2015

(30) Foreign Application Priority Data

Aug. 27, 2012 (KR) ........................ 10-2012-0093936

(51) Int. Cl.
| | | |
|---|---|---|
| C07D 401/04 | (2006.01) |
| C07D 413/14 | (2006.01) |
| A61K 31/4439 | (2006.01) |
| A61K 31/506 | (2006.01) |
| C07D 403/04 | (2006.01) |
| C07D 405/14 | (2006.01) |

(52) U.S. Cl.
CPC ........ *C07D 401/04* (2013.01); *A61K 31/4439* (2013.01); *A61K 31/506* (2013.01); *C07D 403/04* (2013.01); *C07D 405/14* (2013.01); *C07D 413/14* (2013.01)

(58) Field of Classification Search
CPC ... C07D 401/04; C07D 413/14; C07D 405/14
See application file for complete search history.

(56) References Cited

U.S. PATENT DOCUMENTS

| | | |
|---|---|---|
| 5,175,176 A | 12/1992 | Sasse et al. |
| 5,292,744 A | 3/1994 | Sasse et al. |
| 8,637,674 B2 | 1/2014 | Bae et al. |
| 2012/0232117 A1 | 9/2012 | Bae et al. |

FOREIGN PATENT DOCUMENTS

| | | | |
|---|---|---|---|
| EP | 1 900 728 A1 | 3/2008 |
| EP | 2 050 745 A1 | 4/2009 |
| JP | 2003-335672 A | 11/2003 |
| KR | 2003-0027709 A | 4/2003 |
| KR | 10-2004-0094464 A | 11/2004 |
| KR | 10-2011-0025149 A | 3/2011 |
| WO | 93/07138 A1 | 4/1993 |
| WO | WO 2009119987 A2 * | 10/2009 | ........... A61K 31/415 |

OTHER PUBLICATIONS

Bae (KR Oct. 2011-0025149), copy with machine translation provided. Also cited as D1 on international search report.*
Wilson, Polycystic Kidney Disease, 2004, N Engl J Med, 350:2, pp. 151-164.*
Mattos et al., Disease Activity in systemic lupus erythematosus patients with end-stage renal disease: systemic review of the literature, 2012, Clinc Rheumatol, 31, 897-905.*
Reidy et al., Molecular mechanisms of diabetic kidney disease, 2014, The Journal of Clinical Investigation, vol. 124, No. 6, pp. 2333-2340.*
Yu-Feng et al., "Expression of renal nuclear factor-kappaB, transforming growth factor-beta and fibronectin of rats exposed to lead," *Chinese Journal of Industrial Hygiene and Occupational Diseases* 24(3):139-142, 2006, Abstract Only, 1 page.
Extended European Search Report, dated Feb. 5, 2016, for corresponding European Application No. 13834243.1-1453 / 288032, 12 pages.
Boyle et al., "Osteoclast differentiation and activation," *Nature* 423:337-342, 2003.
CAPLUS, Accession No. 1994:106997, "Preparation of pyrazole derivatives and agrochemical fungicides," 30 pages.
CAPLUS, Accession No. 1995:339446, "Preparation of pyrazole derivatives as agricultural and horticultural fungicides," 4 pages.
CAS Registry No. 1187849-40-6, "3H-Pyrazol-3-one, 2,4-dihydro-5-(3-methoxyphenyl)-2-(2-pyridinyl)—$C_{15}H_{13}N_3O_2$," Apr. 2, 2014, 10 pages.
CAS Registry No. 1270043-84-9, "1H-Pyrazol-5-ol, 3-[(2-naphthalenylozy)methyl]-1-(2-pyridinyl)—$C_{19}H_{15}N_3O_2$," Sep. 2, 2015, 29 pages.
CAS Registry No. 1270083-83-4, "1H-Pyrazol-5-ol, 3-(4-bromophenyl)-1-(2-pyridinyl)—$C_{14}H_{10}BR N_3 O$," Apr. 2, 2014, 22 pages.
CAS Registry No. 1270083-87-8, "1H-Pyrazol-5-ol, 3-(3-iodophenyl)-1-(2-pyridinyl)—$C_{14}H_{10}I N_3 O$," Sep. 16, 2016, 33 pages.
CAS Registry No. 1270084-03-1, "1H-Pyrazol-5-ol, 3-(4-bromophenyl)-1-(2-pyridinyl)-, 5-acetate $C_{16}H_{12}Br N_3O_2$," Apr. 2, 2014, 22 pages.
CAS Registry No. 1270084-50-8, "1H-Pyrazol-5-ol, 3-[4-(1,3-benzodioxol-5-yl)phenyl]-1-(2-pyridinyl)—$C_{21}H_{15}N_3O_3$," Apr. 2, 2014, 22 pages.

(Continued)

*Primary Examiner* — Jeffrey S Lundgren
*Assistant Examiner* — Meghan Finn
(74) *Attorney, Agent, or Firm* — Seed IP Law Group LLP

(57) ABSTRACT

The present invention provides a composition for preventing or treating kidney disease, the composition comprising a pyrazole derivative compound or a pharmaceutically acceptable salt thereof; and the composition of the present invention is effective in reducing proteinuria, reducing cell formation between glomerular blood vessels and suppressing kidney fibrosis.

4 Claims, 8 Drawing Sheets

(56) References Cited

OTHER PUBLICATIONS

CAS Registry No. 1270084-88-2, "1H-Pyrazol-5-ol, 3-[1,1'-biphenyl]-4-yl-1-(2-pyrimidinyl)—$C_{19}H_{14}N_4$ O," Apr. 2, 2014, 19 pages.

CAS Registry No. 1270084-92-8, "1H-Pyrazol-5-ol, 3-phenyl-4-propyl-1-(2-pyridinyl)—$C_{17}H_{17}N_3$ O," Sep. 21, 2016, 24 pages.

Darden et al., "Osteoclastic Superoxide Production and Bone Resorption: Stimulation and Inhibition by Modulators of NADPH Oxidase," *Journal of Bone and Mineral Research* 11(5):671-675, 1996.

Fraser et al., "Hydrogen Peroxide, But Not Superoxide, Stimulates Bone Resorption in Mouse Calvariae," *Bone* 19(3):223-226, 1996.

Li et al., "Role of NADPH oxidase in diabetic nephropathy," *International Journal of Internal Medicine* 36(2):93-97, 2009. (with Partial English Translation).

Office Action, dated Oct. 9, 2016, for Chinese Application No. 201380056244.5, 13 pages. (with English Translation).

Oikawa et al., "Meldrum's Acid in Organic Synthesis. 2. A General and Versatile Synthesis of β-Keto Esters," *J. Org. Chem.* 43(10):2087-2088, 1978.

Park et al., "Introduction of N-Containing Heterocycles into Pyrazole by Nucleophilic Aromatic Substitution," *Synthetic Communications* 34(9):1541-1550, 2004.

Park et al., "Identification of antitumor activity of pyrazole oxime ethers," *Bioorganic & Medicinal Chemistry Letters* 15:3307-3312, 2005.

Yang et al., "Nicotinamide Adenine Dinucleotide Phosphate Oxidase in the Formation of Superoxide in Osteoclasts," *Calcif Tissue Int* 63:346-350, 1998.

Yang et al., "A New Superoxide-generating Oxidase in Murine Osteoclasts," *The Journal of Biological Chemistry* 276(8):5452-5458, 2001.

Almansa et al., "Synthesis and Structure-Activity Relationship of a New Series of Potent $AT_1$ Selective Angiotensin II Receptor Antagonists: 5-(Biphenyl-4-ylmethyl)pyrazoles," *J. Med. Chem.* 40:547-558, 1997.

Sawyer et al., "Synthesis and Activity of New Aryl- and Heteroaryl-Substituted Pyrazole Inhibitors of the Transforming Growth Factor-β Type I Receptor Kinase Domain," *J. Med. Chem.* 46(19):3953-3956, Sep. 2003.

\* cited by examiner

COMPOSITION FOR TREATING KIDNEY DISEASE COMPRISING PYRAZOLE DERIVATIVE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310179_408USPC_SEQUENCE_LISTING.txt. The text file is 3.3 KB, was created on Feb. 26, 2015, and is being submitted electronically via EFS-Web.

TECHNICAL FIELD

The present invention relates to a composition for the prevention or treatment of kidney disease, comprising a pyrazole derivative.

BACKGROUND ART

Patients with chronic kidney disease (CKD) are at 10-fold higher risk of cardiovascular disease incidence and mortality than an age control group, and have recently increased in a geometric progression (Schieppati A, Remuzzi G: Chronic renal diseases as a public health problem: epidemiology, social, and economic implications. Kidney Int Suppl. 98:S7-S10, 2005(1)).

CKD is characterized by epithelial-to-mesenchymal transition (EMT) and accumulation of extracellular matrix (ECM) proteins, and exhibits various pathological traits including basement membrane thickening of glomerular capillaries, glomerular mesangial expansion, renal tubular interstitial fibrosis, glomerular hypertrophy and nephromegaly, and proteinuria. Transforming growth factor-β1 (TGF-β1), a factor implicated in renal fibrosis, serves as a final mediator in the production of extracellular matrix proteins in response to various stimuli and thus is regarded as a fibrosis indicator (Qian Y, Feldman E, Pennathur S, Kretzler M, Brosius F C 3rd: From fibrosis to sclerosis: mechanisms of glomerulosclerosis in diabetic nephropathy. Diabetes. 57: 1439-45, 2008).

Diabetic kidney disease (DKD), which is a kind of CKD, is the most common cause of end-stage renal disease (ESRD) (U.S. Renal Data System, USRDS 2011 Annual Data Report: Atlas of End-Stage Renal Disease in the United States, National Institutes of Health, National Institute of Diabetes and Digestive and Kidney Diseases, Bethesda, Md., 2011).

Treatment modalities, known thus far, for restraining the progression of CKD including DKD to end-stage renal disease include the throughgoing control of blood pressure and the use of renin-angiotensin system (RAS) blocker, but there is still a need for a therapeutic agent that guarantees perfect nephroprotective effect (Zhang M Z, Wang S, Yang S, Yang H, Fan X, Takahashi T, Harris R C: The Role of Blood Pressure and the Renin-Angiotensin System in Development of Diabetic Nephropathy (DN) in eNOS−/− db/db Mice. Am J Physiol Renal Physiol. Epub ahead of print, 2011).

DISCLOSURE

Technical Problem

Leading to the present invention, thorough and intensive research of the present inventors into nephroprotection, resulted in the finding that specific pyrazole derivatives have suppressive effects on proteinurea, glomerular mesangial expansion, and renal fibrosis, and can be applied to the protection or treatment of kidney diseases.

It is an object of the present invention to provide a composition of the prevention or treatment of kidney disease, comprising a pyrazole derivative.

It is another object of the present invention to provide a method for preventing or treating kidney disease by administering the pyrazole derivative of the present invention, and use of the pyrazole derivative of the present invention in preparing a pharmaceutical formulation for the prevention or treatment of kidney disease.

Technical Solution

In accordance with an aspect thereof, the present invention provides a composition for the prevention or treatment of kidney disease, comprising a compound selected from among the following compounds, or a pharmaceutically acceptable salt thereof:
1-(pyridin-2-yl)-3-phenyl-4-propyl-1H-pyrazol-5-ol;
1-(pyridin-2-yl)-3-phenyl-4-propyl-1H-pyrazol-5-ol hydrochloride (1-(pyridin-2-yl)-3-phenyl-4-propyl-1H-pyrazol-5-ol.HCl);
3-(3-methoxyphenyl)-1-(pyridin-2-yl)-1H-pyrazol-5(4H)-one;
3-(4-bromophenyl)-1-(pyridin-2-yl)-1H-pyrazol-5-ol;
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol;
3-(2-(benzo[d][1,3]dioxol-5-yl)phenyl)-1-(pyridin-2-yl)-1H-pyrazol-5-ol;
3-(biphenyl-4-yl)-1-(pyrimidin-2-yl)-1H-pyrazol-5-ol; and
3-{2-(4-hydroxy-3-methoxyphenyl)vinyl}-4-propyl-1-(2-pyridinyl)pyrazol-5-ol.

In one exemplary embodiment thereof, the present invention provides a composition for the prevention or treatment of kidney disease, comprising a compound selected among from the following compounds, or a pharmaceutically acceptable salt thereof:
1-(pyridin-2-yl)-3-phenyl-4-propyl-1H-pyrazol-5-ol.HCl;
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol; and
3-(biphenyl-4-yl)-1-(pyrimidin-2-yl)-1H-pyrazol-5-ol.

As used herein, the term "pharmaceutically acceptable salt" refers to a salt typically used in the medicinal field. Examples of the pharmaceutically acceptable salt include inorganic acid salts prepared from, for example, hydrochloride, nitric acid, phosphoric acid, bromic acid, iodic acid, perchloric acid, stanic acid, and sulfuric acid, organic acid salts prepared from, for example, acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanilic acid, hydroiodic acid, etc., and sulfonates prepared from, for example, methane sulfonic acid, ethane sulfonic acid, benzene sulfonic acid, p-toluene sulfonic acid, naphthalene sulfonic acid, etc., but are not limited thereto. Preferable is hydrochloride.

In the present invention, the kidney disease may include diabetic kidney disease, hypertensive nephropathy, glomerulonephritis, pyelonephritis, interstitial nephritis, lupus nephritis, polycystic kidney disease or renal failure.

The kidney disease may be characterized by proteinuria, glomerular sclerosis, or renal interstitial fibrosis.

To the extent of not degrading the effect of the present invention, the composition of the present invention may further comprise a pharmaceutically acceptable additive such as a diluent, a binder, a disintegrant, a lubricant, a pH-adjusting agent, an antioxidant, a solubilizer, etc.

As the diluent, sugar, starch, microcrystalline cellulose, lactose (lactose hydrate), glucose, D-mannitol, alginate, alkaline earth metal salts, clay, polyethylene glycol, anhydrous calcium hydrogen phosphate, or a combination thereof may be used. As the binder, starch, microcrystalline cellulose, highly dispersable silica, mannitol, D-mannitol, sucrose, lactose hydrate, polyethylene glycol, polyvinylpyrrolidone (Povidone), polyvinylpyrrolidone copolymer (copovidone), hypromellose, hydroxypropyl cellulose, natural gum, synthetic gum, copovidone, gelatin, or a combination thereof may be used.

As the disintegrant, starch or modified starch, such as sodium starch glycolate, corn starch, potato starch, pregelatinized starch, etc.; clay such as bentonite, montmorillonite, veegum, etc.; celluloses such as microcrystalline cellulose, hydroxypropyl cellulose, carboxymethyl cellulose; alginic acid or a salt thereof such as sodium alginate; crosslinked celluloses such as croscarmellose sodium; gums such as guar gum, xanthan gum, etc.; crosslinked polymers such as crosslinked polyvinyl pyrrolidone (crospovidone), etc.; effervescent agents such as sodium bicarbonate, citric acid, etc., or a combination thereof may be used.

As the lubricant, talc, stearic acid, magnesium stearate, calcium stearate, sodium laurylsulfate, hydrogenated vegetable oil, sodium benzoate, sodium stearyl fumarate, glyceryl vehenate, glyceryl monooleate, glycerylmonostearate, glyceryl palmitostearate, colloidal silica, or a combination thereof may be used.

As pH-adjusting agent, an acidifier such as acetic acid, adipic acid, ascorbic acid, sodium ascorbate, sodium etherate, malic acid, succinic acid, tartaric acid, fumaric acid, citric acid, etc., and an alkalinizer such as precipitated calcium carbonate, ammonia water, meglumin, sodium carbonate, magnesium oxide, magnesium carbonate, sodium citrate, tribasic calcium phosphate, etc., may be used.

As the antioxidant, dibutyl hydroxy toluene, butyrated hydroxyanisole, tocopherol acetate, tocopherol, propyl galate, sodium hydrogen sulfite, and sodium pyrosulfite etc., may be used. In the immediate-release compartment of the present invention, as the solubilizer, sodium lauryl sulfate, polyoxyethylene sorbitan fatty acid ester (such as polysorbate), docusate sodium, poloxamer etc., may be used.

Moreover, in order to prepare a delayed-release formulation, the composition of the present invention may include an enteric polymer, a water-insoluble polymer, a hydrophobic compound, and a hydrophilic polymer.

The enteric polymer refers to a polymer which is insoluble or stable under acidic conditions of less than pH 5 and is dissolved or degraded under specific pH conditions of pH 5 or higher. For example, the enteric polymer may be enteric cellulose derivatives such as hypromellose acetate succinate, hypromellose phthalate (hydroxypropylmethylcellulose phthalate), hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethyl cellulose, ethylhydroxyethyl cellulose phthalate, and methyl hydroxyethyl cellulose; enteric acrylic acid copolymers such as a styrene-acrylic acid copolymer, a methyl acrylate-acrylic acid copolymer, a methyl acrylate-methacrylic acid copolymer (e.g., Acryl-EZE), a butyl acrylate-styrene-acrylic acid copolymer, and a methyl acrylate-methacrylic acid-octyl acrylate copolymer; enteric polymethacrylate copolymers such as a poly(methacrylic acid/methyl methacrylate) copolymer (e.g., Eudragit L or Eudragit S, manufactured by Evonik, Germany), and a poly(methacrylic acid/ethyl acrylate) copolymer (e.g., Eudragit L100-55); or enteric maleic acid copolymers such as a vinyl acetate-maleic anhydride copolymer, a styrene-maleic anhydride copolymer, a styrene-maleic monoester copolymer, a vinyl methyl ether-maleic anhydride copolymer, an ethylene-maleic anhydride copolymer, a vinyl butyl ether-maleic anhydride copolymer, an acrylonitrile-methyl acrylate-maleic anhydride copolymer, and a butyl acrylate-styrene-maleic anhydride copolymer; and enteric polyvinyl derivatives such as polyvinyl alcohol phthalate, polyvinylacetal phthalate, polyvinylbutyrate phthalate, and polyvinylacetacetal phthalate.

The water-insoluble polymer refers to a pharmaceutically acceptable, water-insoluble polymer that controls the release of a drug. For example, the water-insoluble polymer may be polyvinyl acetate (e.g. Kollicoat SR30D), a water-insoluble polymethacrylate copolymer [for example, poly(ethyl acrylate-methyl methacrylate) copolymer (e.g., Eudragit NE30D), a poly(ethyl acrylate-methyl methacrylate-trimethyl aminoethyl methacrylate) copolymer (e.g., Eudragit RSPO), etc.], ethyl cellulose, cellulose ester, cellulose ether, cellulose acylate, cellulose diacylate, cellulose triacylate, cellulose acetate, cellulose diacetate, cellulose triacetate, etc.

The hydrophobic compound refers to a pharmaceutically acceptable, water-insoluble substance that controls the release of a drug. For example, the hydrophobic compound may be fatty acids and fatty acid esters such as glyceryl palmitostearate, glyceryl stearate, glyceryl behenate, cetyl palmitate, glyceryl monooleate and stearic acid; fatty acid alcohols such as cetostearyl alcohol, cetyl alcohol and stearyl alcohol; waxes such as carnauba wax, beeswax and microcrystalline wax; and inorganic substance such as talc, precipitated calcium carbonate, calcium hydrogen phosphate, zinc oxide, titanium oxide, kaolin, bentonite, montmorillonite and veegum.

The hydrophilic polymer refers to a pharmaceutically acceptable, water-soluble polymer that controls the release of a drug. For example, the hydrophilic polymer may be saccharides such as dextrin, polydextrin, dextran, pectin and a pectin derivative, alginate, polygalacturonic acid, xylan, arabinoxylan, arabinogalactan, starch, hydroxypropyl starch, amylose and amylopectin; cellulose derivatives such as hypromellose, hydroxypropylcellulose, hydroxymethylcellulose, hydroxyethylcellulose, methylcellulose, and sodium carboxymethylcellulose; gums such as guar gum, locust bean gum, tragacanth, carrageenan, gum acacia, gum arabic, gellan gum and xanthan gum; proteins such as gelatin, casein and zein; polyvinyl derivatives such as polyvinyl alcohol, polyvinylpyrrolidone and polyvinylacetal diethylaminoacetate; hydrophilic polymethacrylate copolymers such as a poly(butyl methacrylate-(2-dimethylaminoethyl)methacrylate-methyl methacrylate) copolymer (e.g. Eudragit E100, manufactured by Evonik, Germany), and a poly(ethyl acrylate-methyl methacrylate-triethylaminoethylmethacrylate chloride) copolymer (e.g. Eudragit RL and RS, manufactured by Evonik, Germany); polyethylene derivatives such as polyethylene glycol, and polyethylene oxide; and carbomer.

In addition, the composition of the present invention may be formulated with the use of pharmaceutically acceptable additives such as various additives selected from colorants and fragrances.

In the present invention, the range of the additive that can be used in the present invention is not limited to the above-mentioned additives, the additive may be appropriately selected by those skilled in the art and the composition may be formulated with the use of the above-mentioned additives in a conventional dose.

The pharmaceutical composition in accordance with the present invention may be formulated into oral dosage forms such as powders, granules, tablets, capsules, suspensions, emulsions, syrups, and aerosols, medicines for external use, suppositories or sterile injection solutions, using a conventional method, and may be used.

In accordance with another aspect thereof, the present invention provides a method for preventing or treating kidney disease, comprising administering to a subject including a mammal a composition for the prevention or treatment of kidney disease comprising a compound selected from among the following compounds, or a pharmaceutically acceptable salt thereof:
1-(pyridin-2-yl)-3-phenyl-4-propyl-1H-pyrazol-5-ol;
1-(pyridin-2-yl)-3-phenyl-4-propyl-1H-pyrazol-5-ol.HCl;
3-(3-methoxyphenyl)-1-(pyridin-2-yl)-1H-pyrazol-5(4H)-one;
3-(4-bromophenyl)-1-(pyridin-2-yl)-1H-pyrazol-5-ol;
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol;
3-(2-(benzo[d][1,3]dioxol-5-yl)phenyl)-1-(pyridin-2-yl)-1H-pyrazol-5-ol;
3-(biphenyl-4-yl)-1-(pyrimidin-2-yl)-1H-pyrazol-5-ol; and
3-{2-(4-hydroxy-3-methoxyphenyl)vinyl}-4-propyl-1-(2-pyridinyl)pyrazol-5-ol.

As used herein, the term "administering" means the introduction of the composition for preventing and treating kidney disease in accordance with the present invention to a patient by any appropriate method. So long as it allows the composition for preventing and treating kidney disease in accordance with the present invention to reach a target tissue, any route via which the composition is administered may be taken. For example, the composition may be administered orally, intraperitoneally, intravenously, intramuscularly, subcutaneously, intradermally, intranasally, intrapulmonary, rectally, intracavitary, intraperitoneally, or intrathecally, but not limited thereto.

The administration of the composition for preventing or treating kidney diseases in accordance with the present invention may be conducted once a day, or two or more times a day at regular intervals of time.

The effective dose level of the compound selected from among the following compounds or a pharmaceutically acceptable salt thereof may vary depending on a variety of factors including the patient's weight, age, gender, general health, and diet, the time of administration, the route of administration, and the rate of excretion, and the severity of disease:
1-(pyridin-2-yl)-3-phenyl-4-propyl-1H-pyrazol-5-ol;
1-(pyridin-2-yl)-3-phenyl-4-propyl-1H-pyrazol-5-ol.HCl;
3-(3-methoxyphenyl)-1-(pyridin-2-yl)-1H-pyrazol-5(4H)-one;
3-(4-bromophenyl)-1-(pyridin-2-yl)-1H-pyrazol-5-ol;
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol;
3-(2-(benzo[d][1,3]dioxol-5-yl)phenyl)-1-(pyridin-2-yl)-1H-pyrazol-5-ol;
3-(biphenyl-4-yl)-1-(pyrimidin-2-yl)-1H-pyrazol-5-ol; and
3-{2-(4-hydroxy-3-methoxyphenyl)vinyl}-4-propyl-1-(2-pyridinyl)pyrazol-5-ol.

For example, dosages may range from 0.1 to 100 mg/kg/day, which may vary depending on the severity of disease, and patient's age, sex, etc.

In accordance with a further aspect thereof, the present invention provides a method for preventing or treating kidney disease, comprising administering to a subject including a mammal a composition for the prevention or treatment of kidney disease comprising a compound selected from among the following compounds, or a pharmaceutically acceptable salt thereof:
1-(pyridin-2-yl)-3-phenyl-4-propyl-1H-pyrazol-5-ol.HCl;
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol; and
3-(biphenyl-4-yl)-1-(pyrimidin-2-yl)-1H-pyrazol-5-ol.

In accordance with a still further aspect thereof, the present invention provides use of the following compounds or a pharmaceutically acceptable salt thereof in preparing a pharmaceutical formulation for the prevention or treatment of kidney disease:
1-(pyridin-2-yl)-3-phenyl-4-propyl-1H-pyrazol-5-ol;
1-(pyridin-2-yl)-3-phenyl-4-propyl-1H-pyrazol-5-ol.HCl;
3-(3-methoxyphenyl)-1-(pyridin-2-yl)-1H-pyrazol-5(4H)-one;
3-(4-bromophenyl)-1-(pyridin-2-yl)-1H-pyrazol-5-ol;
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol;
3-(2-(benzo[d][1,3]dioxol-5-yl)phenyl)-1-(pyridin-2-yl)-1H-pyrazol-5-ol;
3-(biphenyl-4-yl)-1-(pyrimidin-2-yl)-1H-pyrazol-5-ol; and
3-{2-(4-hydroxy-3-methoxyphenyl)vinyl}-4-propyl-1-(2-pyridinyl)pyrazol-5-ol.

In an exemplary embodiment thereof, the present invention provides use of the following compounds or a pharmaceutically acceptable salt thereof in preparing a pharmaceutical formulation for the prevention or treatment of kidney disease:
1-(pyridin-2-yl)-3-phenyl-4-propyl-1H-pyrazol-5-ol.HCl);
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol; and
3-(biphenyl-4-yl)-1-(pyrimidin-2-yl)-1H-pyrazol-5-ol.

Advantageous Effects

Having suppressive effects on proteinuria, glomerular hypertrophy, and renal fibrosis, the compounds of the present invention, or pharmaceutically acceptable salts thereof, can be used in preventing or treating kidney disease.

BEST MODE

Figure 1:
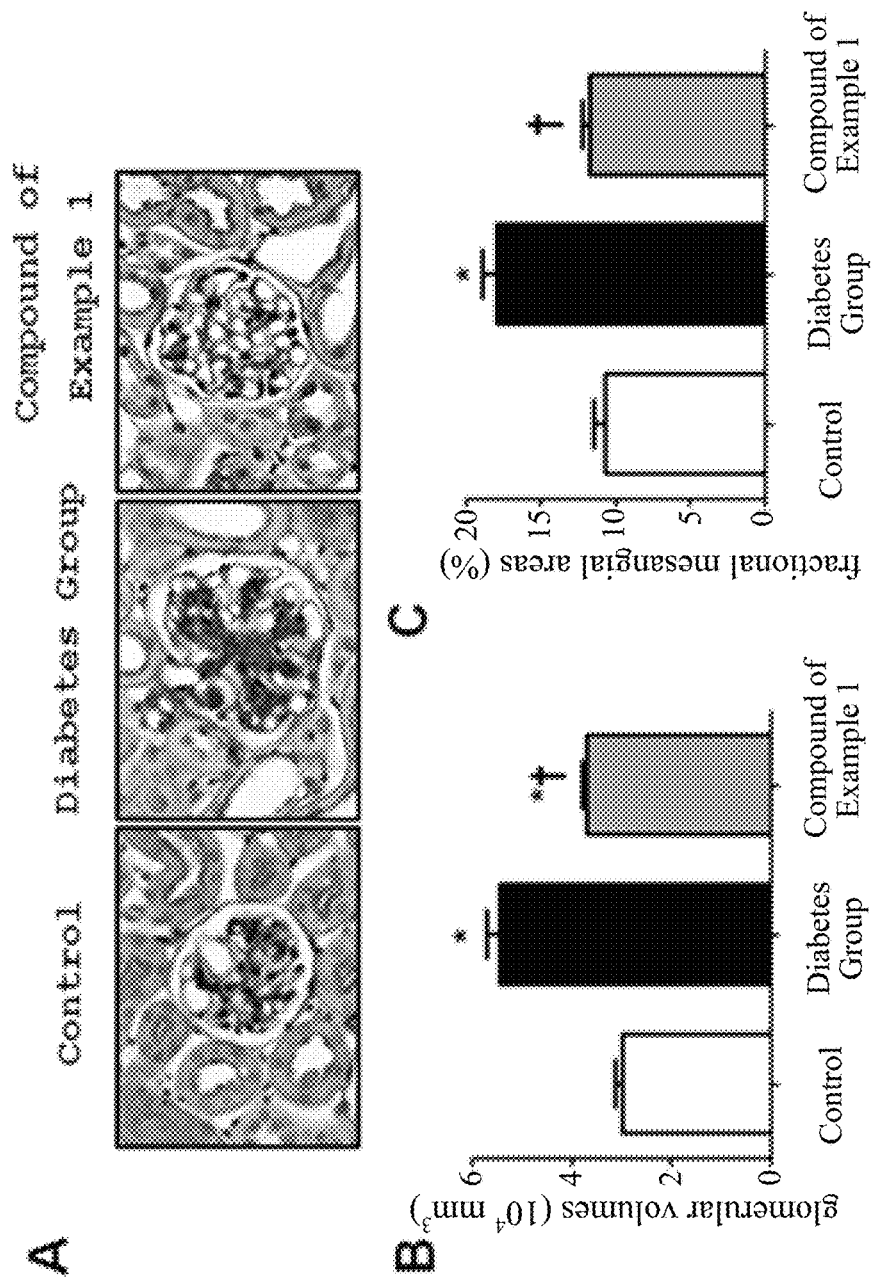
FIG. 1A-C shows the effect of the compound of Example 1 on glomerular hypertrophy and glomerular mesangial expansion.

A better understanding of the present invention may be obtained through the following examples that are set forth to illustrate, but are not to be construed as the limit of the present invention. Unless specifically stated otherwise, reagents and solvents mentioned below were purchased from Sigma-Aldrich Korea, Alfa Aesar, or Tokyo Chemical Industry (TCI). Data was obtained using Eclipse FT 300 MHz Spectrometer, JEOL for $^1$H-NMR and $^{13}$C-NMR, and MStation JMS 700 mass Spectrometer for Mass.

Example 1

Synthesis of 1-(Pyridin-2-yl)-3-Phenyl-4-Propyl-1H-Pyrazol-5-ol.HCL (Hereinafter Referred to as Compound 18-278)

Step 1: Synthesis of 1-(pyridin-2-yl)-3-phenyl-4-propyl-1H-pyrazol-5-ol[1-(pyridin-2-yl)-3-phenyl-4-propyl-1H-pyrazol-5-ol]

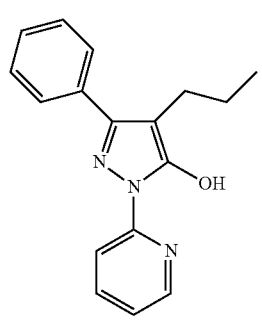

[Chemical Formula 1]

2-propyl-3-oxo-3-phenylpropionic acid ethyl ester (2.52 g, 10.7 mmol) and ethanol (10 mL) were placed in a round-bottom flask, and 2-hydrazinopyridine (1.29 g, 11.8 mmol) diluted with ethanol (10 mL) was slowly added dropwise at 0° C. The resulting solution was heated under reflux at 100° C. for 3 days. The solvent was removed by distillation under reduced pressure, and the resulting solid was washed with hexane and ethyl acetate and dried under vacuum to give the compound of Chemical Formula 1 in 82% yield.

$^1$H NMR (300 MHz, CDCl$_3$) δ 12.50 (1H, s), 8.27-8.25 (1H, m), 8.01 (1H, d, J=8.5 Hz), 7.81 (1H, m), 7.69 (2H, m), 7.48-7.34 (3H, m), 7.14-7.10 (1H, m), 2.54 (2H, d, J=7.5 Hz), 1.64 (2H, m), 0.93 (3H, t, J=7.3 Hz);

EIMS (70 e V) m/z (rel intensity) 279 (M+, 37), 250 (100).

Step 2: Synthesis of 1-(pyridin-2-yl)-3-phenyl-4-propyl-1H-pyrazol-5-ol.HCl (278)

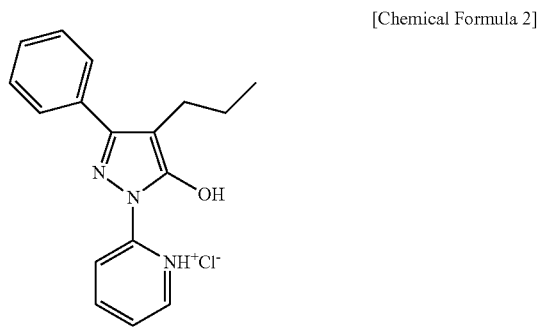

[Chemical Formula 2]

1-(pyridin-2-yl)-3-phenyl-4-propyl-1H-pyrazol-5-ol (280 mg) prepared in step 1 was dissolved in ethyl ether (4 mL) in a round-bottom flask, and ethyl ether (0.55 mL) in which 2 M HCl was dissolved was slowly added dropwise at 0° C. The solvent was removed by vacuum filtration, and the resulting solid was washed with hexane and ethyl acetate and dried under vacuum to give 270 mg of the compound of Chemical Formula 2.

$^1$H NMR (300 MHz, DMSO-d$_6$) δ 8.44 (1H, d, J=4.2 Hz), 8.0 8-8.03 (2H, m), 7.66-7.64 (2H, m), 7.48-7.42 (3H, m), 7.34-7.30 (1H, m), 2.49 (2H, brs), 2.43 (2H, t, J=7.5 Hz), 1.48 (2H, m), 0.48 (3H, t, J=7.3 Hz).

Example 2

Synthesis of 3-(3-Methoxyphenyl)-1-(Pyridin-2-yl)-1H-Pyrazol-5-ol (18-001)

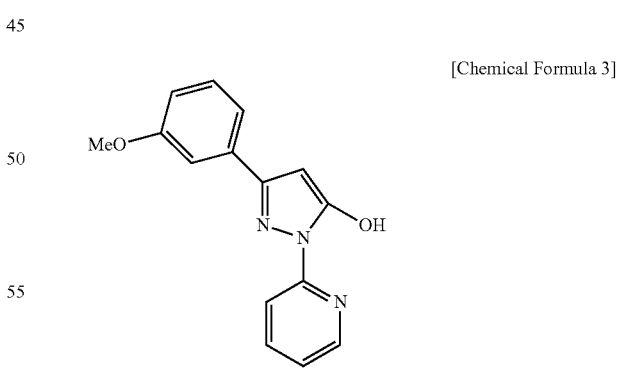

[Chemical Formula 3]

The compound of Chemical Formula 3 was synthesized as disclosed in Korean Patent No. 10-0942382. Briefly, drops of 2-hydrazinopyridine (1.1 equivalents) in 3 ml of ethanol were slowly added to 3-(3-methoxyphenyl)-3-oxo-propionic acid ethyl ester (1 equivalent) and 4 ml of ethanol at 0° C. in a round-bottom flask. The solution was heated under reflux for 20 minutes. After removal of the solvent by distillation under reduced pressure, the solid thus obtained was washed with hexane and ethyl acetate, and dried in a vacuum to afford the compound of Chemical Formula 3: Yield 67%.

[Chemical Formula 3']

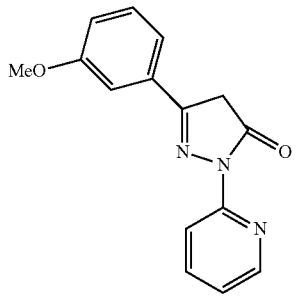

The compound of Chemical Formula 3 is an enol form while the compound of Chemical Formula 3' takes a keto form. These compounds are in keto-enol tautomerism so that they may interconvert to each other.

Example 3

Synthesis of 3(4-Bromophenyl)-1-(Pyridin-2-yl)-1H-Pyrazol-5-ol (Hereinafter Referred to as Compound 18-066)

[Chemical Formula 4]

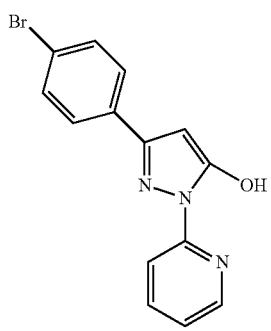

The compound was synthesized as disclosed in Korean Patent Application Publication No. 10-2011-0025149. Briefly, a solution of 2-hydrazinopyridine (10 mmol, manufactured by Aldrich) in ethanol (10 mL) was added to ethyl 4-bromo benzoylacetate (10 mmol, manufactured by Aldrich) and ethanol (10 mL) in a 100 mL round-bottom flask. After stirring at 100° C. for 8 hrs, the solution was cooled at room temperature. The solid thus formed was filtered, washed with ethanol and hexane, and dried in a vacuum to afford the compound of Chemical Formula 4.

Yield: 81% (2.5 g, 8.0 mmol);

$^1$H NMR (300 MHz, CDCl$_3$) δ 12.8 (br, 1H) 8.30-8.28 (m, 1H), 8.03 (d, 1H, J=8.5 Hz), 7.94-7.88 (m, 1H), 7.73 (d, 2H, J=8.6 Hz), 7.54 (d, 2H, J=8.6 Hz), 7.21-7.16 (m, 1H), 5.91 (s, 1H);

EIMS (70 eV) m/z (rel intensity) 315 (M+, 25), 317 (M+, 26), 101 (19), 79 (100).

Example 4

Synthesis of 3-(4-Bromophenyl)-1-(Pyridin-2-yl)-1H-Pyrazol-5-yl Acetate (Hereinafter Referred to as Compound 18-067)

[Chemical Formula 5]

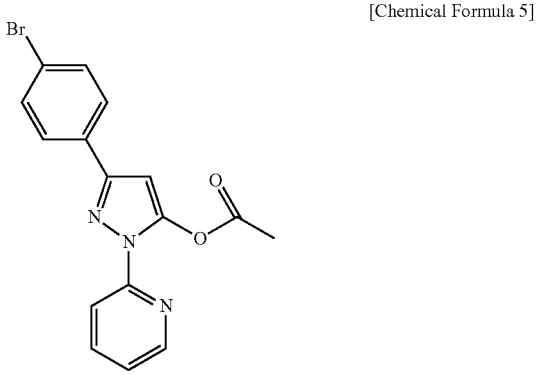 [SMILES: CC(=O)Oc1cc(-c2ccc(Br)cc2)nn1-c1ccccn1]

To a solution of 3-(4-bromophenyl)-1-(pyridin-2-yl)-1H-pyrazol-5-ol (3 mmol, 1 equivalent), synthesized in Example 3, in 10 mL of CHCl$_3$ were added 1.2 equivalents of triethyl amine at 0° C. Then, 1 equivalent of acetyl chloride was added before reflux for 10 min. After completion of the reaction, the solution was mixed with H$_2$O (10 mL) and extracted with CHCl$_3$. The organic layer thus formed was dried over anhydrous MgSO$_4$, filtered, concentrated, and purified by column chromatography (n-Hexane: EA=5:1 (v/v)) to afford the compound of Chemical Formula 5.

Example 5

Synthesis of 3-(3-Iodophenyl)-1-(Pyridin-2-yl)-1H-Pyrazol-5-ol (Hereinafter Referred to as Compound 18-082)

[Chemical Formula 6]

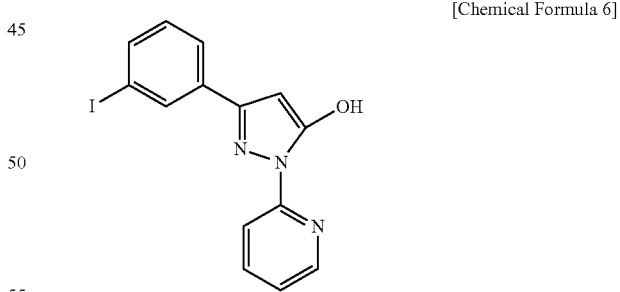

The compound was synthesized as disclosed in Korean Patent Application Publication No. 10-2011-0025149. Briefly, a solution of 2-hydrazinopyridine (10 mmol, manufactured by Aldrich) in ethanol (10 mL) was added to ethyl 3-iodobenzoylacetate (10 mmol, manufactured by Aldrich) and ethanol (10 mL) in a 100 mL round-bottom flask. After stirring at 100° C. for 8 hrs, the solution was cooled at room temperature. The solid thus formed was filtered, washed with ethanol and hexane, and dried in a vacuum to afford the compound of Chemical Formula 6.

Yield: 80.4%

$^1$H NMR (300 MHz, CDCl$_3$) δ 12.84 (br, 1H) 8.31-8.29 (m, 1H), 8.25-8.24 (m, 1H), 8.08-8.04 (m, 1H), 7.95-7.89 (m, 1H), 7.81-7.77 (m, 1H), 7.70-7.66 (m, 1H), 7.23-7.13 (m, 2H), 5.91 (s, 1H).

Example 6

Synthesis of 3-((Naphthalen-3-yloxy)Methyl)-1-(Pyridin-2-yl)-1H-Pyrazol-5-ol (6B) (Hereinafter Referred to as Compound 18-095)

[Chemical Formula 7]

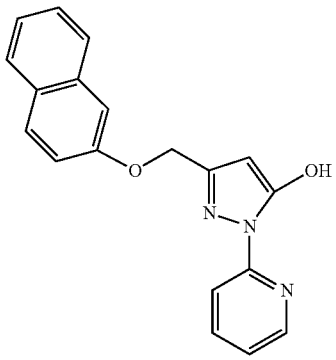

Synthesis was preformed according to the disclosure of Korean Patent Application Publication No. 10-2011-0025151. Briefly, the compound was synthesized according to the following steps 1 and 2.

Step 1: Synthesis of ethyl 4-(naphthalen-3-yloxy)-3-oxobutanoate

In a 25 mL round-bottom flask, oxalyl chloride (0.338 mL, 4.0 mmol, manufactured by Aldrich) was slowly added to a solution of 2-naphthalenoxy acetic acid (4b, 404.4 mg, 2.0 mmol, manufactured by Fluka) in 28 mL of anhydrous benzene, and subjected to reaction in the presence of a small amount of the catalyst DMF at room temperature for 2 hrs while stirring. The reaction mixture was concentrated, and the concentrate was dissolved in methylene chloride.

Subsequently, the solution was cooled to 0° C., and added slowly with a solution of Meldrum's acid (323 mg, 2.24 mmol) in 2 mL of methylene chloride and then with 1 mL of pyridine, and stirred at room temperature for 18 hrs. When the reaction was completed as monitored by TLC, the reaction was stopped with 1.5 mL of 2M HCl and ice. The reaction mixture was washed with saturated brine, dried over anhydrous sodium sulfate, and concentrated. After the solvent was removed by vacuum drying, the residue was dissolved in 30 mL of ethanol, and heated at 60° C. for 20 hrs under reflux, with a cooling condenser installed to the flask. The reaction mixture was concentrated to remove ethanol, and the concentrate was extracted with ethyl acetate, washed with saturated brine, dried over anhydrous sodium sulfate, concentrated and purified by column chromatography (n-Hex/EtOAc=10/1 (v/v)) to afford ethyl 4-(naphthalen-3-yloxy)-3-oxobutanoate.

Yield 61%

Step 2: Synthesis of 3-((naphthalen-3-yloxy)methyl)-1-(pyridin-2-yl)-1H-pyrazol-5-ol In a 25 mL round-bottom flask, a solution of 2-hydrazinopyridine (0.55 g, 5.0 mmol) in 5 mL of ethanol was slowly added to a solution of ethyl 4-(naphthalen-3-yloxy)-3-oxobutanoate (5a, 1.2 g, 5.4 mmol) in 10 mL of ethanol at 100° C. over 30 min, followed by stirring for 20 hrs. When the reaction was completed as monitored by TLC, the reaction mixture was concentrated by evaporation, extracted with ethyl acetate, washed with saturated brine, dried over anhydrous sodium sulfate, concentrated and purified by column chromatography (n-Hex/EtOAc=9/1 (v/v)) to afford the compound of Chemical Formula 7.

Yield 65.2%;

$^1$H NMR (300 MHz, CDCl$_3$) δ 12.76 (br, 1H) 8.29-8.27 (m, 1H), 7.97-7.87 (m, 2H), 7.79-7.74 (m, 3H), 7.49-7.41 (m, 1H), 7.37-7.15 (m, 4H), 5.76 (s, 1H), 5.15 (s, 2H); EIMS m/z (rel intensity) 317 (M+, 100), 174 (99), 106 (7)

Example 7

Synthesis of 3-(2-(Benzo[D][1,3]Dioxol-5-yl)Phenyl)-1-(Pyridin-2-yl)-1H-Pyrazol-5-ol (Hereinafter Referred to as Compound 18-177)

[Chemical Formula 8]

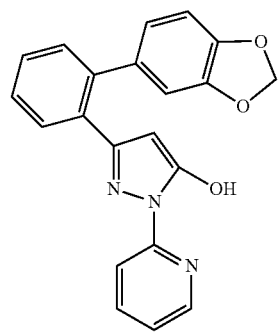

The compound of Chemical Formula 8 was synthesized as disclosed in Korean Patent Application Publication No. 10-2011-0025149.

Example 8

Synthesis of 3-(Biphenyl-4-yl)-1-(Pyrimidin-2-yl)-1H-Pyrazol-5-ol (Hereinafter Referred to as Compound 18-186)

[Chemical Formula 9]

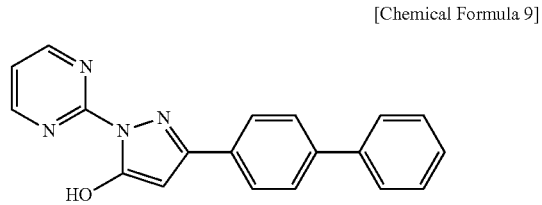 [SMILES: Oc1cc(-c2ccc(-c3ccccc3)cc2)nn1-c1ncccn1]

The compound of Chemical Formula 9 was synthesized as disclosed in Korean Patent Application Publication No. 10-2011-0025149.

Example 9

Synthesis of 3-{2-(4-Hydroxy-3-Methoxyphenyl)Vinyl}-4-Propyl-1-(2-Pyridinyl)Pyrazol-5-ol (Hereinafter Referred to as 18-273)

[Chemical Formula 10]

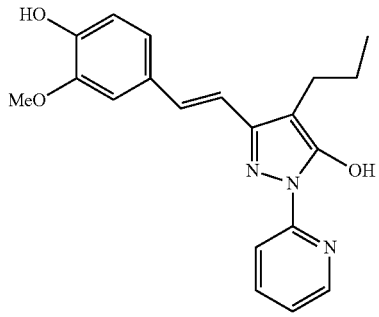

To a solution of (E)-ethyl 5-[4-(tert-butyldimethylsilyloxy)-3-methoxyphenyl]-3-oxo-2-propyl pentanoate (1.02 g, 2.42 mmol) in acetic acid (5 mL) was added 2-hydrazinopyridine (266 mg, 2.44 mmol), followed by stirring for 2 days under heating reflux. The reaction mixture was concentrated by distillation under reduced pressure, and extracted with ethyl acetate (15 mL) and water (5 mL) (×3 times). The organic layer was dried over anhydrous sodium sulfate, and purified by column chromatography [hexane (Hex): ethyl acetate (EtOAc)=15:1] to afford 3-{2-(4-tert-butyldimethylsilyloxy-3-methoxyphenyl)vinyl}-4-propyl-1-(2-pyridinyl)pyrazol-5-ol (676 mg, 69%).

The compound (99 mg, 0.21 mmol) was dissolved in methanol (MeOH) (1 mL), and added with conc. HCl (0.02 mL, 0.25 mmol). The solution was stirred for 1 day, and dried under reduced pressure to obtain a solid. This was dried in a vacuum to afford the compound (74 mg, 98%).

$^1$H NMR (300 MHz, DMSO-$d_6$) δ 8.46 (1H, m), 8.30 (1H, d, J=9.0 Hz), 7.95 (1H, m), 7.43-6.81 (6H, m), 3.72 (3H, s), 2.42 (2H, t, J=7.2 Hz), 1.53 (2H, q, J=9.0 Hz), 0.91 (3H, t, J=9.0 Hz).

Comparative Example

Synthesis of 3-Phenyl-4-Benzyl-5-Benzyloxy-1-(2-Pyridinyl)Pyrazole] (Hereinafter Referred to as Compound 18-233)

[Chemical Formula 11]

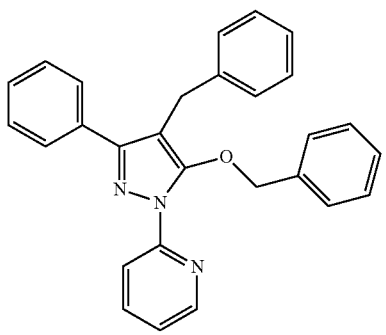

In a 10 mL round-bottom flask, 3-phenyl-4-benzyl-1-(pyridin-2-yl)-1H-pyrazol-5-ol (100 mg, 0.30 mmol), potassium carbonate (58 mg, 0.42 mmol), and DMF (1 mL) were stirred together at room temperature for 10 min. After addition of benzyl bromide (55 μl, 0.46 mmol), stirring was conducted for 2 hrs. H$_2$O (3 mL) was added, followed by extraction with ethyl acetate (3×5 mL) Water was removed with MgSO$_4$, and the residue was filtered. Separation by column chromatography (Hex: EtOAc=2:1) afforded the compound of Chemical Formula 11 (65 mg, 52%).

$^1$H NMR (300 MHz, CDCl$_3$) δ 8.61-8.59 (m, 1H), 8.06 (d, 1H, J=8.3 Hz), 7.80 (t, 1H, J=8.4 Hz), 7.58-7.48 (m, 5H), 7.21-7.07 (m, 7H), 6.96 (d, 2H J=7.9 Hz), 6.55 (d, 2H, J=7.1 Hz), 4.91 (s, 2H), 3.69 (s, 2H); ELMS (70 eV) m/z (rel intensity) 417 (M$^-$, 6), 339 (39), 326 (61), 296 (40), 206 (26), 193 (85), 121 (15), 91 (100)

Example 10

Examination of State Change in Experimental Animal by the Compound of the Present Invention All animal experiments were performed with the approval of the Ewha Womans University Institutional Animal Care and Use Committee. The effects of the compounds of the present invention on type 1 diabetes model were examined. To this end, first, blood glucose levels of C57BL/6J mice, 8 weeks old, were examined after administration of streptozotocin at a dose of 50 mg/kg for 5 days (Hwang I, Lee J, Park J, Huh J Y, Lee H B, Ho Y S, Ha H: Catalase deficiency accelerates diabetic renal injury through peroxisomal dysfunction. Diabetes: 72 8-738, 2012). Then, 1-(pyridin-2-yl)-3-phenyl-4-propyl-1H-pyrazol-5-ol.HCl, the compound of Example 1, was orally administered to the mice at a dose of 10 mg/kg/day for 12 weeks. After 12 weeks of administration, they were sacrificed, and blood samples therefrom were measured for levels of blood glucose, hemoglobin A1c (HbA1c), and plasma creatinine. For urine protein levels, urine samples were taken. The urine protein levels were measured. Levels of blood glucose, HbA1c, plasma creatinine, and urine protein were measured using ONETOUCH Ultra of Johnson & Johnson, DCA2000+ Analyzer of SIEMENS, Detect X Serum Creatinine Detection kit of Arbor Assays, and Bio-Rad protein assay kit of Bio-Rad Laboratories, respectively. The control (WT) stands for a group in which type 1 diabetes mellitus was not induced, the diabetes group (DM) for a group in which type 1 diabetes mellitus was induced, and the treatment group (DM+compound of Example 1) for a group that was treated with the compound of Example 1 after introduction of type 1 diabetes mellitus.

Results of state change of the experimental animals, caused by the compound of the present invention, are summarized in Table 1, below.

TABLE 1

|  | Control (WT) | Diabetes Group (DM) | Treatment Group (DM + Compound of Example 1) |
| --- | --- | --- | --- |
| Body Weight (g) | 30 ± 1 | 22 ± 1* | 23 ± 1* |
| Blood glucose (mg/dl) | 162 ± 11 | 549 ± 13* | 531 ± 21* |
| HbA1c(%) | 4.5 ± 0.1 | 10.0 ± 0.4* | 10.4 ± 0.3* |
| Kidney Weight (g) | 0.19 ± 0.01 | 0.22 ± 0.01* | 0.22 ± 0.01* |
| Kidney Wt./ Body Wt. (g/kg) | 6.3 ± 0.1* | 10.3 ± 0.5* | 9.9 ± 0.5* |

TABLE 1-continued

|  | Control (WT) | Diabetes Group (DM) | Treatment Group (DM + Compound of Example 1) |
|---|---|---|---|
| Plasma creatinine (mg/dl) | 0.19 ± 0.03 | 0.24 ± 0.03 | 0.25 ± 0.04 |
| Urine albumin (relative to control) | 1.00 ± 0.03 | 1.55 ± 0.09* | 1.26 ± 0.04† |

Data of Table 1 are expressed as mean ± standard error (SE) from 8 to 12 mice per group. Statistic comparison among the groups were analyzed by ANOVA and Fisher's least significant difference test, with significance at p < 0.05.
*P < 0.05 vs WT,
†P < 0.05 vs DM As can be seen in Table 1, the diabetes group (DM) decreased in body weight and increased in blood glucose level and hemoglobin A1c level, compared to the control (WT), which indicated that the diabetes group maintained hyperglycemia for 12 weeks after the introduction of type 1 diabetes mellitus. As the diabetes group was found to increase in kidney weight and ratio of kidney weight to body weight, as well, hypertrophy was caused in the diabetes group. In addition, the diabetes group increased in an excretion level of albumin, although not different in plasma creatinine compared to the control. The mice to which 1-(pyridin-2-yl)-3-phenyl-4-propyl-1H-pyrazol-5-ol.HCl, the compound of Example 1, was administered after the induction of diabetes mellitus (treatment group) exhibited no significant differences in body weight, blood glucose, hemoglobin A1c, kidney weight, kidney weight/body weight, and plasma creatinine, compared to the diabetes group, but decreased in urine albumin.

Hence, the compound of the present invention (1-(pyridin-2-yl)-3-phenyl-4-propyl-1H-pyrazol-5-ol.HCl) was found to have a nephroprotective effect as it decreased the diabetic kidney disease-caused proteinuria (excretion of albumin, etc.).

Example 11

Examination of Glomerular Hypertrophy and Glomerular Mesangial Expansion

For morphological analysis for examining glomerular hypertrophy and glomerular mesangial cell formation, a staining method was used as disclosed previously (Lee E A, Seo J Y, Jiang Z, Yu M R, Kwon M K, Ha H, Lee H B: Reactive oxygen species mediate high glucose-induced plasminogen activator inhibitor-1 up-regulation in mesangial cells and in diabetic kidney. Kidney Int. 67:1762-71, 2005).

As described in Example 10, diabetes was induced in mice that were then treated with 1-(pyridin-2-yl)-3-phenyl-4-propyl-1H-pyrazol-5-ol.HCl, the compound of Example 1, and scarified 12 weeks later. After cardiac perfusion with 0.1 M PBS (phosphate-buffered saline), tissue fixation was performed overnight with 2% PLP (paraformaldehyde-lysine-periodate). Paraffin embedding was conducted as follows: sequential treatment with: 70% ethanol for 1 hr; 80% ethanol for 1 hr; 90% ethanol for 1 hr; 95% ethanol for 1 hr, twice; 100% ethanol for 1 hr, three times; xylene for 30 min, twice; paraffin for 30 min; and paraffin for 1.5 hrs. The paraffin tissue was sliced into a section 4 μm thick, followed by PAS (periodic acid-Schiff) staining to detect basement membranes and glycogen deposition. In one renal tissue, 30 glomeruli were scanned, and measured for size and mesangial cell formation, using Image-Pro Plus 4.5 Software (MEDIA CYBERNETICS). The glomerular size was calculated according to Equation 1.

$$\text{Glomerular size} = (\text{Sectional area of glomerulus})^{3/2} \times B/K \quad \text{[Equation 1]}$$

wherein B (=1.38) is a shape factor of a sphere, and k (=1.1) is a particle-size distribution coefficient.

Experiment results are given in FIG. 1. FIG. 1 shows images of glomeruli stained with PAS (periodic acid-Schiff) (A), a graph of glomerular volumes (B), and a graph of fractional mesangial areas (C). In FIG. 1, the control (WT) stands for a group in which type 1 diabetes mellitus was not induced, the diabetes group (DM) for a group in which type 1 diabetes mellitus was induced, and the treatment group (DM+compound of Example 1) for a group that was treated with the compound of Example 1 after introduction of type 1 diabetes mellitus. Data of FIG. 1 are expressed as mean±standard error (SE) from 8 to 12 mice per group. Statistic comparison among the groups was analyzed by ANOVA and Fisher's least significant difference test, with significance at p<0.05. *P<0.05 vs. WT, †P<0.05 vs DM.

Figure 2:
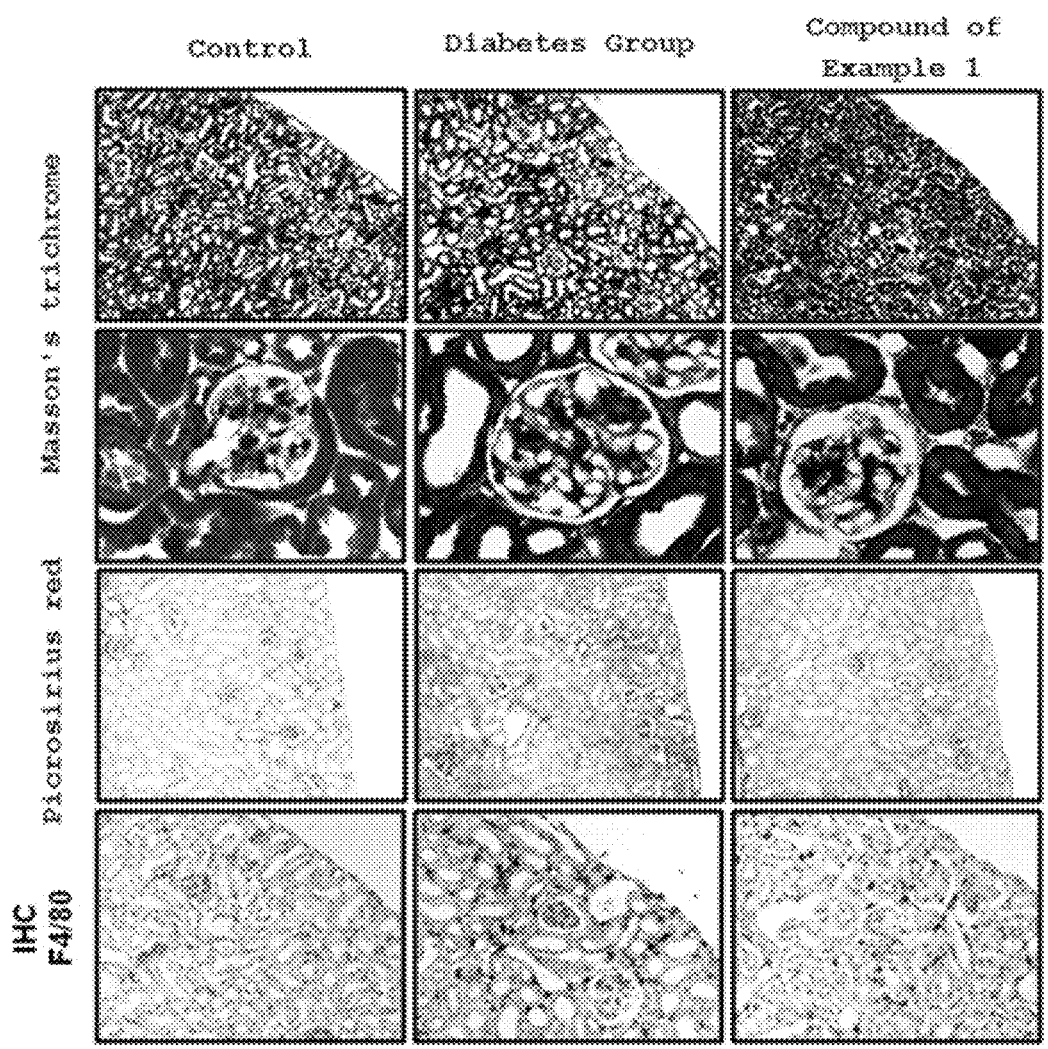
FIG. 2 shows the effect of the compound of Example 1 on collagen accumulation (Masson's trichrome staining, picrosirius red staining), and production of macrophage marker (F4/80).

As can be seen in FIG. 2, the glomerular size of the group treated with the compound of Example 1 increased, compared to the control, but significantly smaller than that of the diabetes group, while glomerular mesangial expansion in the treatment group was reduced to the level of the control, compared to the diabetes group.

These results demonstrated that the compounds of the present invention can prevent renal fibrosis by suppressing the renal mesangial and tubulointerstitial accumulation of collagen through down-regulation of the extracellular matrix collagen Iα1 in proximal tubular cells.

Therefore, the compound of the present invention (1-(pyridin-2-yl)-3-phenyl-4-propyl-1H-pyrazol-5-ol.HCl) was found to have nephroprotective effects by reducing glomerular size and glomerular mesangial expansion in diabetic kidney disease-induced animal models.

Example 12

Examination of Suppression of Collagen Accumulation and Reduction of Macrophage

Immunohistochemical Staining

Immunohistochemical staining was performed as previously disclosed (Noh H, Kim J S, Han K-H, Lee G T, Song J S, Chung S H, Jeon J S, Ha H, Lee H B: Oxidative stress during peritoneal dialysis: implications in functional and structural changes in the membrane. Kidney Int. 69: 2022-2028, 2006).

Briefly, as described in Example 11, diabetes was induced in mice that were then treated with 1-(pyridin-2-yl)-3-phenyl-4-propyl-1H-pyrazol-5-ol.HCl, the compound of Example 1, and scarified 12 weeks later. After cardiac perfusion with 0.1 M PBS (phosphate-buffered saline), tissue fixation was performed overnight with 2% PLP (paraformaldehyde-lysine-periodate). Paraffin embedding was conducted by sequential treatment with: 70% ethanol for 1 hr; 80% ethanol for 1 hr; 90% ethanol for 1 hr; 95% ethanol for 1 hr, twice; 100% ethanol for 1 hr, three times; xylene for 30 min, twice; paraffin for 30 min; and paraffin for 1.5 hrs. The paraffin tissue was sliced into a section 4 μm thick, followed by deparaffinization with alcohol. In order to enhance antibody penetration thereinto, the renal tissue was immersed in 10 mM citrate buffer (pH 6.0), heated with microwaves (at 700 watts for 5 min and then at 100 watts for 5 min), and then finally incubated at room temperature for 30 min Intrinsic peroxidase was removed by treatment with peroxidase blocking reagent (Peroxidase Blocking Reagent Ready-To-Use, Dakocytomation) for 30 min. Subsequently, the renal tissue was incubated with a protein block serum-free solution (Protein Blocking Serum-Free Ready-To-Use, Dakocytomation) for 15 min and then overnight with a primary antibody (F4/80, Santa Cruz) at 4° C., followed by amplification with ABC kit (Santa Cruz) using the ABC (avidin-biotin-enzyme complex) method. Color was developed with a liquid DAB substrate chromogen system (Dakocytomation) before observation under an optical microscope.

Masson's Trichrome and Picrosirius Red Staining

To examine tissue injury, staining was performed with Masson's trichrome (Sigma-Aldrich) and picrosirius red (Sigma-Aldrich) according to the manufacturer's instructions. The degree of tissue injury was expressed as tubulointerstitial collagen accumulation per area.

Results of immunohistochemical staining (IHC F4/80), Masson's trichrome staining, and picrosirius red staining are shown in FIG. 2. In FIG. 2, The control (WT) stands for a group in which type 1 diabetes mellitus was not induced, the diabetes group (DM) for a group in which type 1 diabetes mellitus was induced, and the treatment group (DM+compound of Example 1) for a group that was treated with the compound of Example 1 after introduction of type 1 diabetes mellitus. The black dots in the IHC F4/80 panels of FIG. 2 represent the expression of F4/80 while collagen accumulation is represented by blue and red colors in the panels of Masson's trichrome and picrosirius red, respectively.

As can be seen in FIG. 2, more abundant blue sites were visualized in the diabetes group than in the control as stained with Masson's trichrome. The group treated with the compound of Example 1 was visualized blue by Masson's trichrome staining in a smaller area than was the diabetes group. Picrosirius red staining visualized the diabetes group in red in a larger area, compared to the control while a smaller area of the group treated with the compound of Example 1 was visualized in red, compared to the diabetes group. Turning to immunohistochemical staining (F4/80), a larger area of the diabetes group was visualized in black, compared to the control. In addition, the group treated with the compound of Example 1 was stained in black in a smaller area than was the diabetes group.

Accordingly, Masson's trichrome staining and picrosirius red staining, both designed to examine extracellular matrix accumulation, indicated greater collagen accumulation in the diabetes group than in the control. Also, more abundant macrophages were detected in the diabetes group than in the control as demonstrated by immunohistochemical staining (F4/80). In contrast, the administration of the compound of Example 1, 1-(pyridin-2-yl)-3-phenyl-4-propyl-1H-pyrazol-5-ol.HCl, to diabetes-induced mice (the treatment group of the compound of Example 1) significantly reduced collagen accumulation and macrophage production (F4/80).

Hence, the compound (1-(pyridin-2-yl)-3-phenyl-4-propyl-1H-pyrazol-5-ol.HCl) according to the present invention was found to inhibit collagen accumulation and reduce macrophage (F4.80) production in diabetic kidney disease-induced animal models, thus exhibiting nephroprotective effects.

Example 13

Examination of Suppression Renal Fibrosis
[Real-Time PCR (Polymerase Chain Reaction) Analysis]

Total RNA was isolated using Trizol reagent (Invitrogen) according to the manufacturer's instruction. The total RNA isolate was used for real-time PCR.

Briefly, as described in Example 10, diabetes was induced, and 1-(pyridin-2-yl)-3-phenyl-4-propyl-1H-pyrazol-5-ol.HCl, the compound of Example 1 of the present invention, was administered to the mice that were sacrificed 12 weeks later. Then, renal tissues were excised from the mice and homogenized with a predetermined amount (500 µl) of Trizol reagent (Invitrogen), followed by centrifuging the homogenate (13,000 rpm, 10 min). The supernatant was reacted with 200 µl of chloroform for 15 min and centrifuged. The total RNA was precipitated with isopropyl alcohol, and washed with 75% ethyl alcohol before use in experiments. From 2 µg of total RNA, cDNA was synthesized using a reverse transcription kit (Applied Biosystems), and selective mRNA was quantitatively analyzed in ABI 7300 real-time PCR thermal cycler (Applied Biosystems) with the aid of SYBR Green PCR Master Mix kit according to the manufacturer's instruction. Each experiment was run in duplicate with 20 µl. For correct quantitation and identification of results from a single product, a standard curve and a dissociation curve were employed. PCR was performed with 40 thermal cycles of 95° C. for 15 sec and 56° C. for 1 min. Sets of primers for amplifying genes of interest were synthesized in Bionia (Daejeon, Korea) as shown in Table 2. Real-time PCR results are shown in FIG. 3.

TABLE 2

| Gene | Forward Primer Sequence | SEQ. ID. No. | Reverse Primer Sequence | SEQ. ID. No. |
|---|---|---|---|---|
| Collagen Iα1 | 5'-CGGATAGCAGATTG AGAACATCCG-3' | 1 | 5'-CGGCTGAGTACGGAA CACACA-3' | 2 |
| Collagen IV | 5'-CACGAGCTTCCCTGG TAGTCGTG-3' | 3 | 5'-GGACAACCTTTGCTG CCTCA-3' | 4 |
| F4/80 | 5'-CTGTAACCGGATGG CAAACT-3' | 5 | 5'-ATGGCCAAGGCAAG ACATAC-3' | 6 |
| Fibronectin | 5'-CGGCGTATGCTGTCA CTGGCCG-3' | 7 | 5'-AAGTTGAAGGCAGCC ACCTG-3' | 8 |
| TGF-β1 | 5'-GGACTCTCCACCTGC AAGAC-3' | 9 | 5'-GACTGGCGAGCCTTA GTTTG-3' | 10 |
| 18S rRNA | 5'-CGAAAGCATTTGCC AAGAAT-3' | 11 | 5'-AGTCGGCATCGTTTA TGGTC-3' | 12 |

Figure 3:
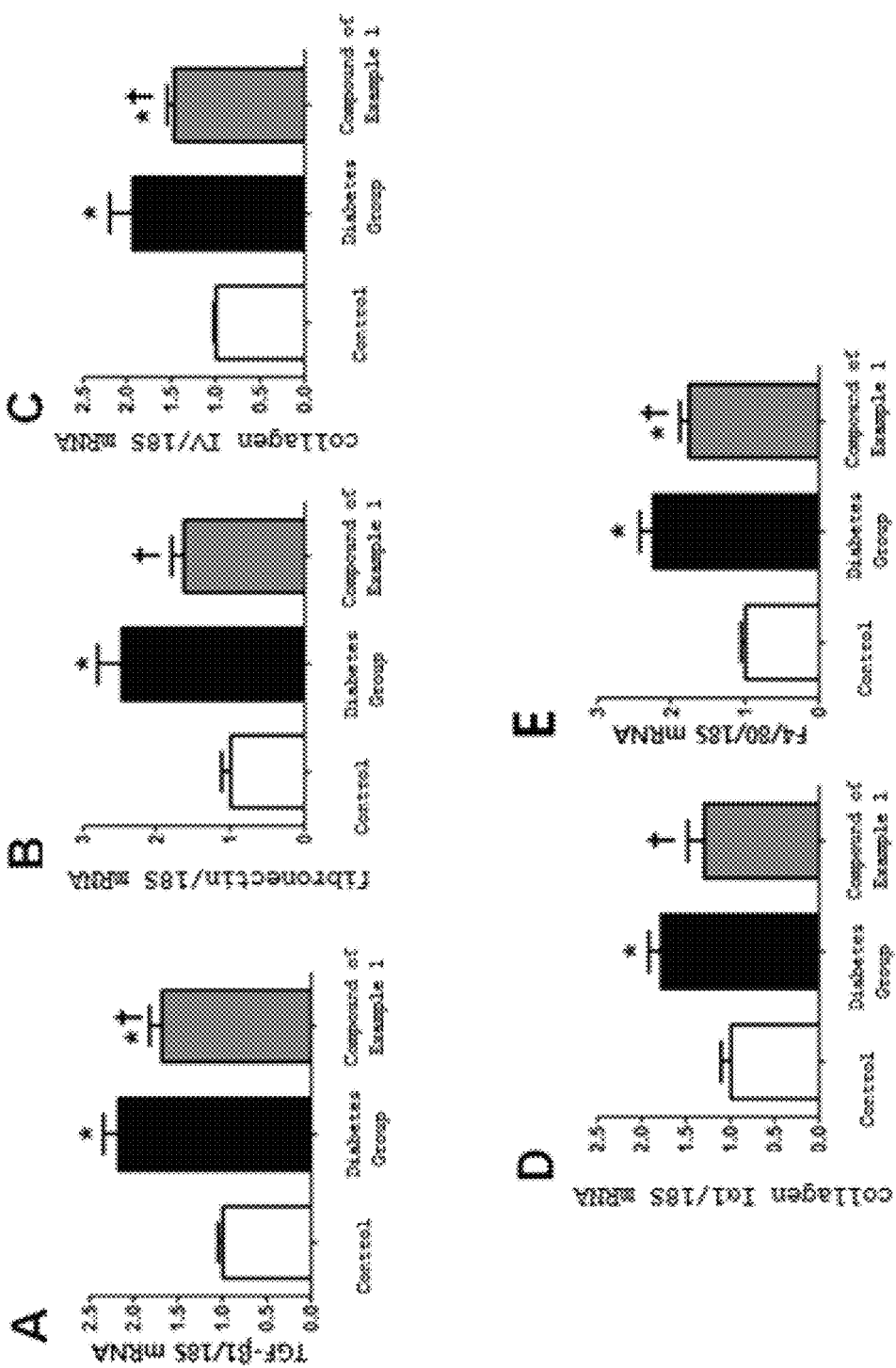
FIG. 3A-E shows the effect of the compound of Example 1 on the expression of transforming growth factor-β1 (TGF-β1), extracellular matrix proteins (fibronectin, collagen IV, and collagen Iα1), and inflammatory factor (F4/80).
Figure 4:
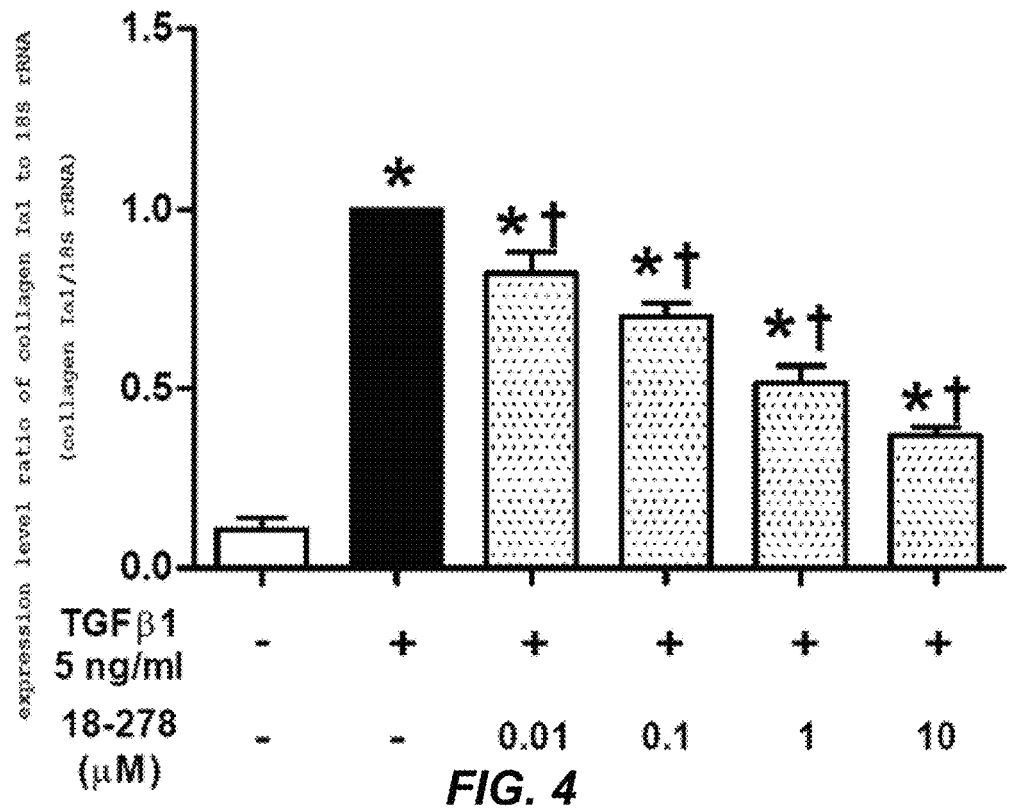
FIGS. 4 to 13 show the inhibitory effects of compounds of Examples 1 to 9 and Comparative Example 1 on collagen Iα1 expression in proximal tubular cells.
Figure 5:
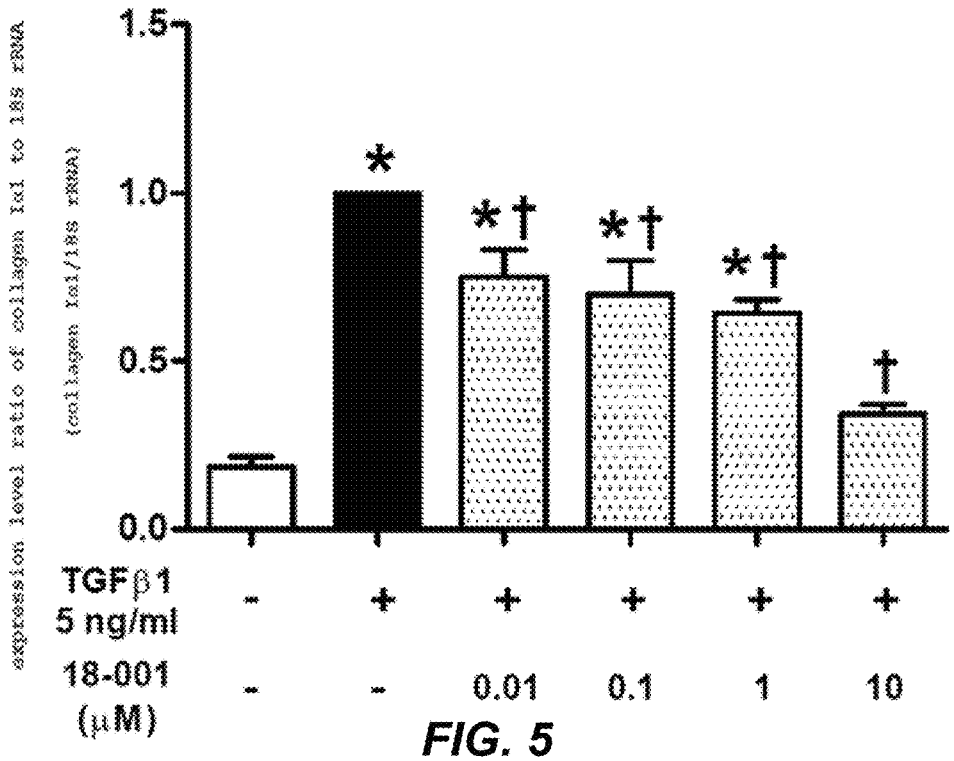
Figure 6:
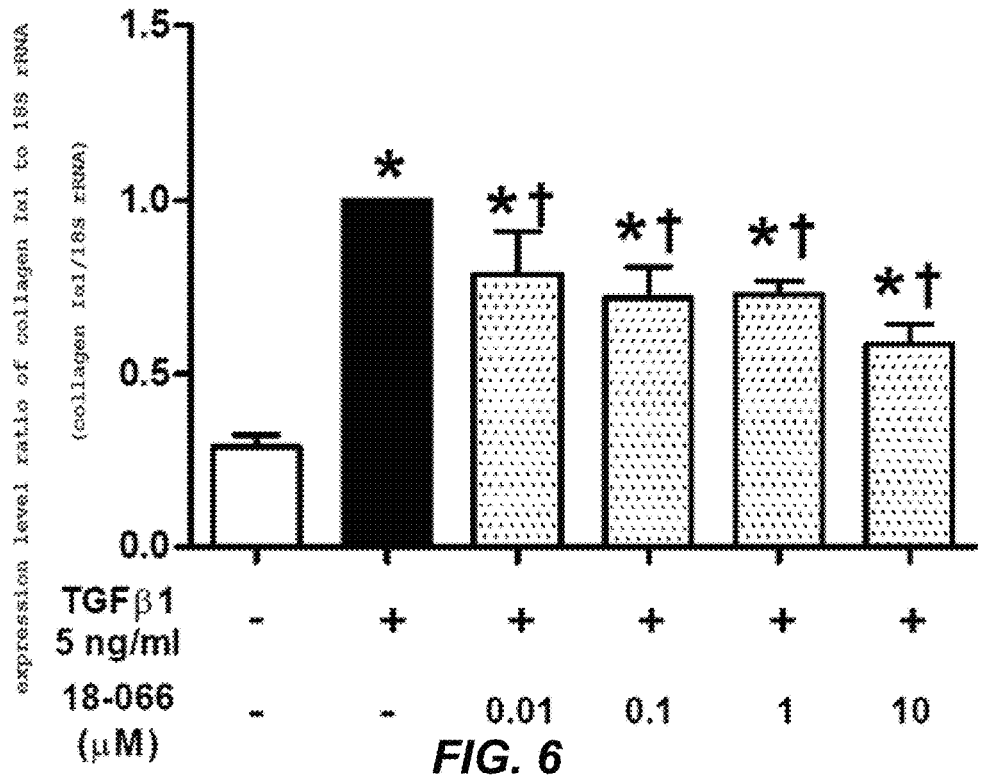
Figure 7:
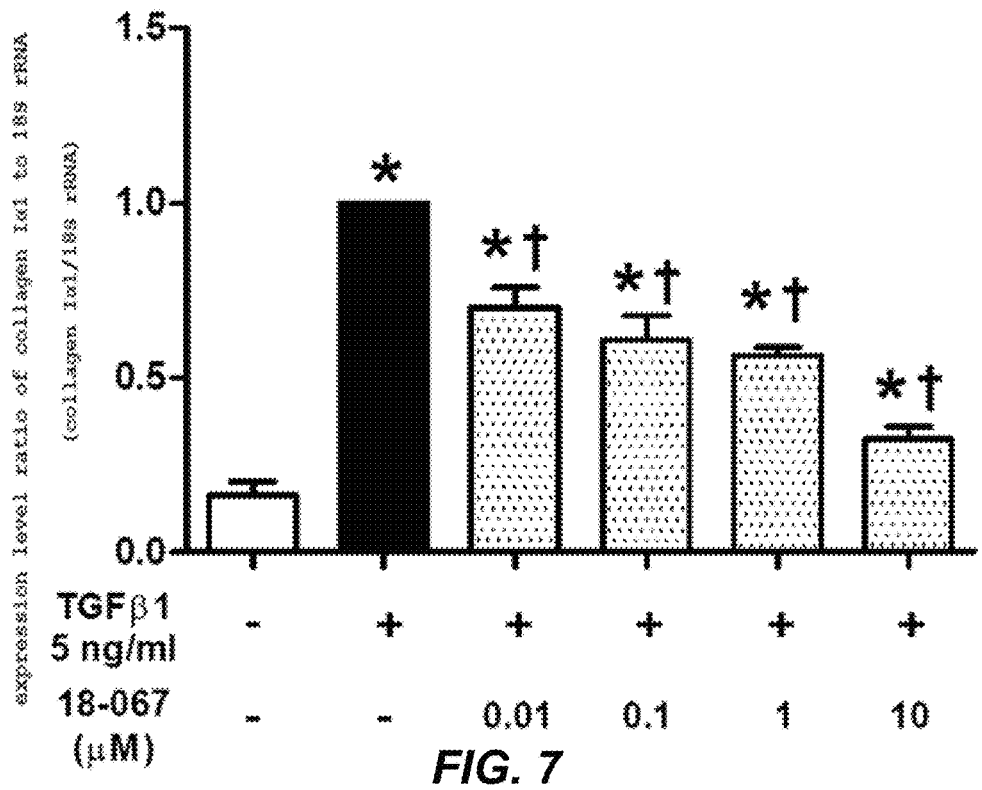
Figure 8:
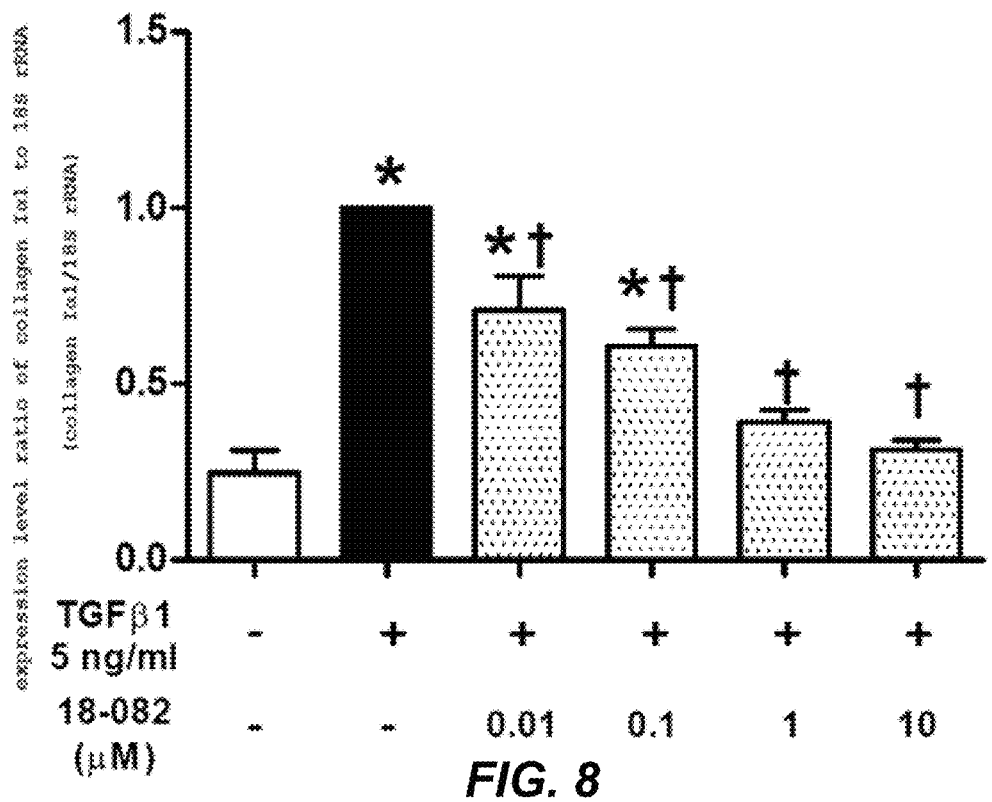
Figure 9:
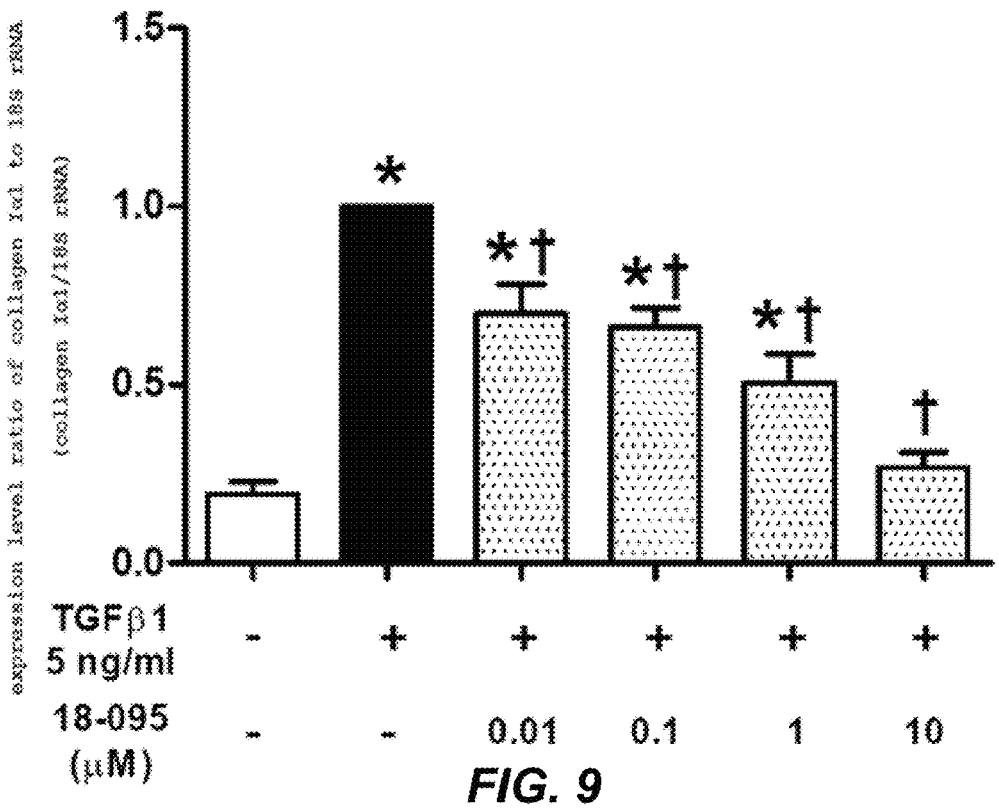
Figure 10:
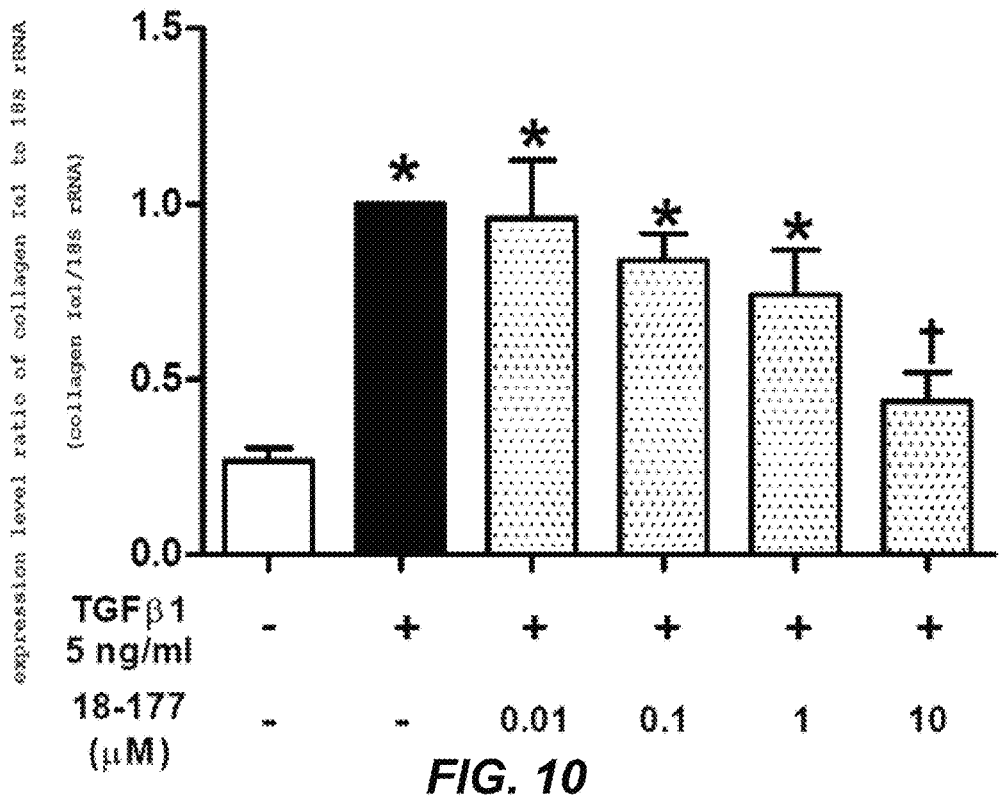
Figure 11:
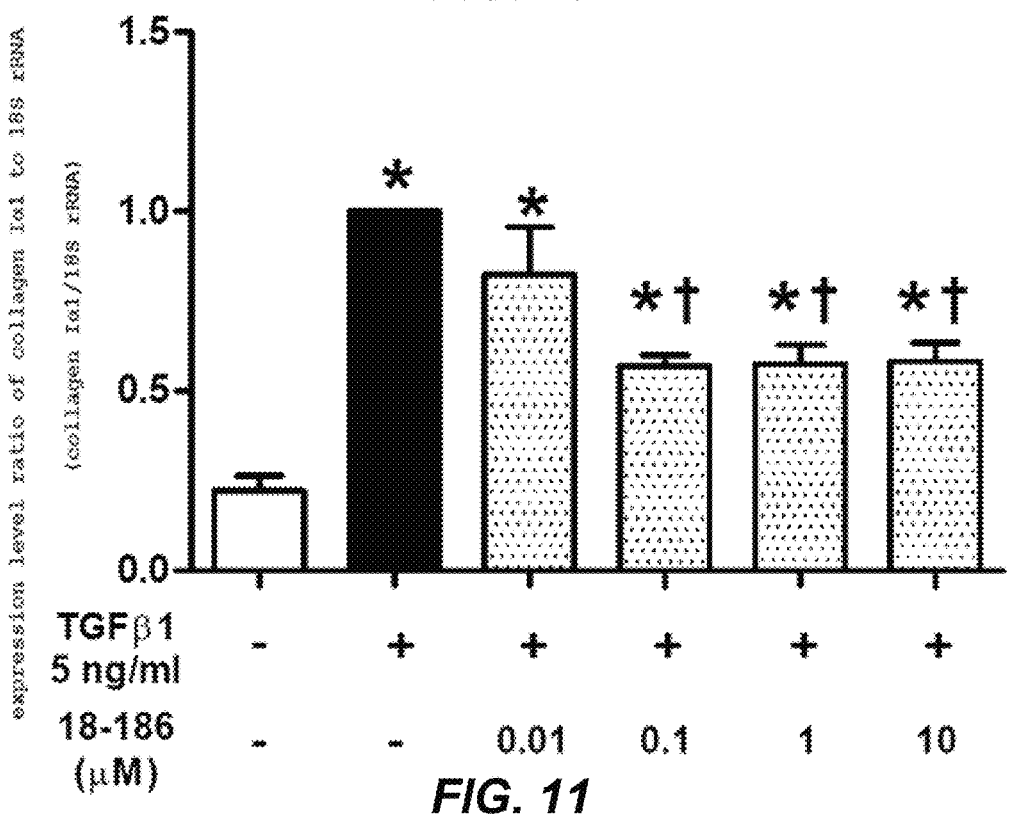
Figure 12:
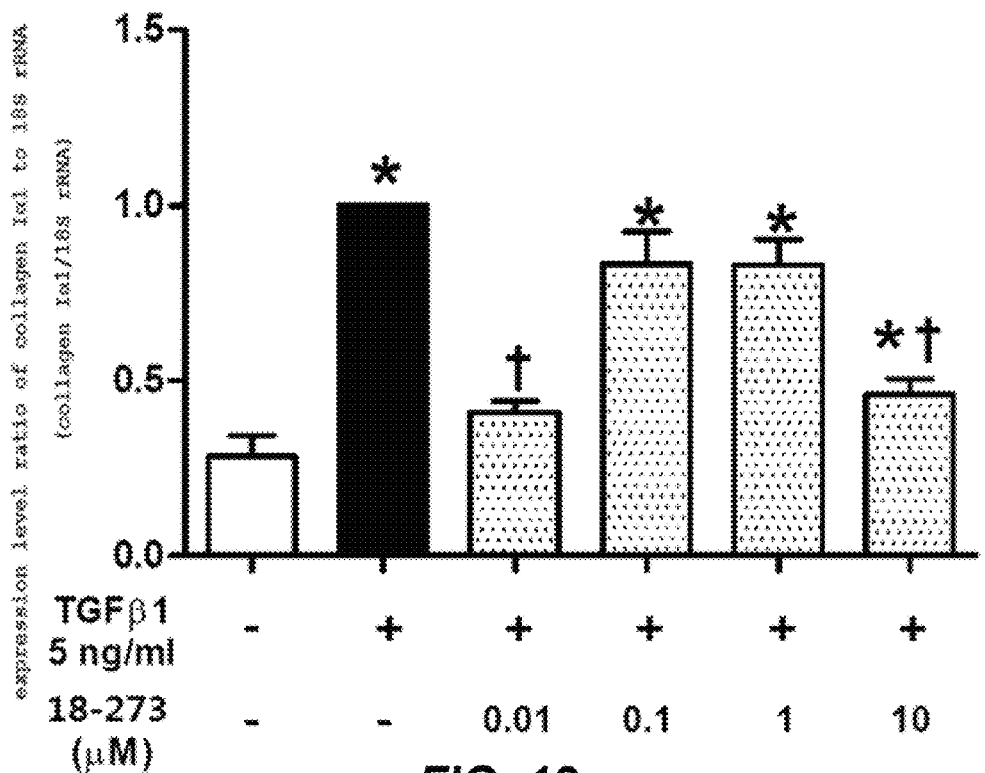
Figure 13:
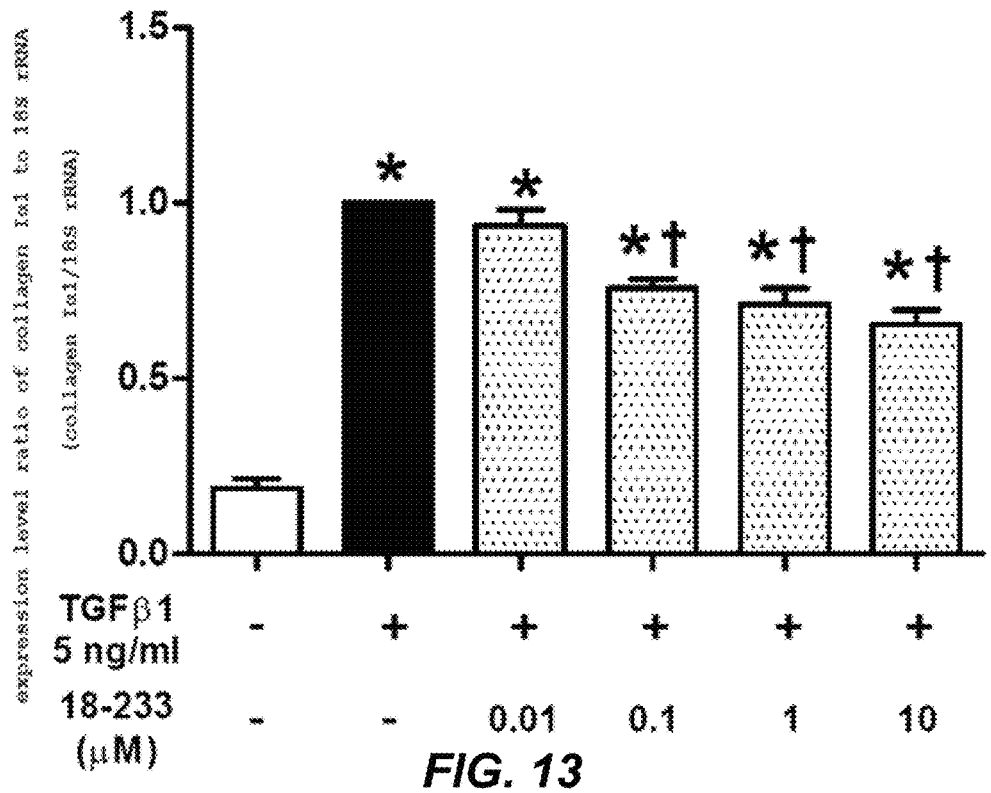

FIG. 3 shows graphs of expression level ratios of TGF-β1 mRNA to 18S rRNA (A), expression level ratios of fibronectin mRNA to 18S rRNA (B), expression level ratios of collagen IV mRNA to 18S rRNA (C), expression level ratios of Collagen Iα1 mRNA to 18S rRNA (D), and expression level ratios of F4/80 mRNA to 18S rRNA (E). In FIG. 3, the control (WT) stands for a group in which type 1 diabetes mellitus was not induced, the diabetes group (DM) for a group in which type 1 diabetes mellitus was induced, and the treatment group (DM+compound of Example 1) for a group that was treated with the compound of Example 1 after introduction of type 1 diabetes mellitus. Data of FIG. 3 are expressed as mean±standard error (SE) from 8 to 12 mice per group. Statistic comparison among the groups was analyzed by ANOVA and Fisher's least significant difference test, with significance at p<0.05. *P<0.05 vs. WT, †P<0.05 vs. DM.

As can be seen in FIG. 3, the diabetes-induced mice to which 1-(pyridin-2-yl)-3-phenyl-4-propyl-1H-pyrazol-5-ol-.HCl, the compound of Example 1 of the present invention, was administered (the treatment group of the compound of Example 1) significantly decreased in the expression levels of TGF-β1, a factor related to renal fibrosis, and fibronectin, collagen Iα1, collagen IV, well known as extracellular matrix proteins, and the inflammatory factor F4/80, compared to the diabetes group.

Accordingly, the compound (1-(pyridin-2-yl)-3-phenyl-4-propyl-1H-pyrazol-5-ol.HCl) according to the present invention was found to have a nephroprotective effect as it inhibited renal fibrosis.

Example 14

Examination of Inhibitory Effect of the Compound on Collagen Iα1 Expression in Proximal Tubular Cell mProx24, which is a name of the proximal tubular cells derived from proximal tubule segments obtained by finely sectioning the kidney of adult C57BL6/J mice, was granted from Professor Sugaya, St. Marianna University School of Medicine, Kanagawa, Japan. mProx24 was cultured in DMEM (Dulbecco's modified Eagle's medium) supplemented with 10% fetal calf serum (FCS, Gibco), 100 U/ml penicillin, 100 μg/ml streptomycin, and 44 mM NaHCO$_3$ at 37° C. in a 5% CO$_2$ atmosphere. For quantitation of RNA expression, the cells were cultured in 6-well plates. When the cells grew 90% confluent, the medium was changed with a fresh 0.15% FCS (Gibco)-supplemented DMEM. Incubation in this medium for 24 hrs halted the cell growth to synchronize the growth cycle in the cells. Compounds of Examples 1 to 9 and Comparative Example were respectively dissolved in DMSO (dimethylsulfoxide) to form a concentration of 50 mM, and subjected to serial dilution to 10 mM, 1 mM, 0.1 mM, and 0.01 mM. 10 mM, 1 mM, 0.1 mM, and 0.01 mM solutions of each of the compounds of Examples 1 to 9 and Comparative Example were 1,000-fold diluted in 0.15% FCS (Gibco)-supplemented DMEM to form final concentrations of 10 μM, 1 μM, 0.1 μM, and 0.01 μM, respectively. In addition, 0 μM (DMSO 1 μL) was used. The cells were incubated for 1 hr in the dilutions and then for 6 hrs in the presence of 5 ng/ml recombinant human transforming growth factor-β1 (hTGF-β1, R&D Systems). For the control, hTGF-β1 was not used. Total RNA was extracted from mProx24 using Trizol (Invitrogen). For quantitation of mRNA expression, a reaction volume of 20 μL including cDNA transcripts, primer pairs, and SYBR Green PCR Master Mix (Applied Biosystems) was subjected to real-time PCR with the aid of StepOnePlus (Applied Biosystems) (real-time PCR condition: 95° C., 10 min→40 thermal cycles of denaturation at 95° C. for 15 sec and primer annealing at 60° C. for 1 min→95° C. for 15 sec, 60° C. for 1 min, and 95° C. for 15 sec to measure a melting curve). Quantitation was normalized to 18S rRNA expression level. A pair of primers for mouse collagen Iα1 were 5'-GAACATCACCTACCACTGCA-3'(SEQ ID NO: 13) and 5'-GTTGGGATGGAGGGAGTTTA-3' (SEQ ID NO: 14). Forward and reverse primers for mouse r18S rRNA were 5'-CGA AAG CAT TTG CCA AGA AT-3' (SEQ ID NO: 11) and 5'-AGT CGG CAT CGT TTA TGG TC-3' (SEQ ID NO: 12), respectively.

Experiment results are given in Tables 3 to 12 and FIGS. 4 to 13. Tables 3 to 12 and FIGS. 4 to 13 show inhibitory effects of the compounds of Examples 1 to 9 and Comparative Example 1 on collagen Iα1 expression in proximal tubular cells.

Data of Tables 3 to 12 and FIGS. 4 to 13 are measurements of experiments repeated three to five times for each concentration, and are expressed as mean±standard error (SE). Statistic comparison among the groups was analyzed by ANOVA and Fisher's least significant difference test, with significance at p<0.05. *P<0.05 vs. WT, †P<0.05 vs. DM.

In Tables 3 to 12, mean values of expression level ratios of collagen Iα1 (Col1α) to 18S rRNA (18S), and % inhibition against collagen Iα1 expression for each group are shown, together with IC$_{50}$ value (μM). In this regard, % inhibition means relative inhibition to 100% for the control and 0% for the group that was treated with hTGF-β1 but not with any of the compounds of Examples or Comparative Example.

FIGS. 4 to 13 shows expression level ratios of collagen Iα1 (Col1α) to 18S rRNA (18S) (relative increase) for each group.

TABLE 3

| 18-278 | Mean | SE | expression inhibition rate (%) |
|---|---|---|---|
| Control | 0.107 | 0.034 | 100.00 |
| 0 | 1 | 0 | 0.00 |
| 0.01 | 0.821 | 0.058 | 20.04 |
| 0.1 | 0.701 | 0.037 | 33.48 |
| 1 | 0.516 | 0.049 | 54.20 |
| 10 | 0.369 | 0.026 | 70.66 |
| IC$_{50}$ | | 0.742 | |

TABLE 4

| 18-001 | Mean | SE | expression inhibition rate (%) |
|---|---|---|---|
| Control | 0.186 | 0.029 | 100.00 |
| 0 | 1.000 | 0 | 0.00 |
| 0.01 | 0.748 | 0.084 | 30.96 |
| 0.1 | 0.698 | 0.1 | 37.10 |
| 1 | 0.642 | 0.04 | 43.98 |
| 10 | 0.345 | 0.025 | 80.47 |
| IC$_{50}$ | | 3.191 | |

TABLE 5

| 18-066 | Mean | SE | expression inhibition rate (%) |
|---|---|---|---|
| Control | 0.289 | 0.035 | 100.00 |
| 0 | 1 | 0 | 0.00 |
| 0.01 | 0.785 | 0.123 | 30.24 |
| 0.1 | 0.717 | 0.089 | 39.80 |
| 1 | 0.726 | 0.04 | 38.54 |
| 10 | 0.583 | 0.059 | 58.65 |
| IC$_{50}$ | | 2.137 | |

TABLE 6

| 18-067 | Mean | SE | expression inhibition rate (%) |
|---|---|---|---|
| Control | 0.164 | 0.037 | 100.00 |
| 0 | 1.000 | 0 | 0.00 |
| 0.01 | 0.700 | 0.06 | 35.59 |
| 0.1 | 0.607 | 0.071 | 46.62 |
| 1 | 0.562 | 0.025 | 51.96 |
| 10 | 0.325 | 0.035 | 80.07 |
| IC$_{50}$ | | 0.299 | |

TABLE 7

| 18-082 | Mean | SE | expression inhibition rate (%) |
|---|---|---|---|
| Control | 0.246 | 0.065 | 100.00 |
| 0 | 1.000 | 0 | 0.00 |
| 0.01 | 0.710 | 0.097 | 39.51 |
| 0.1 | 0.605 | 0.051 | 53.81 |
| 1 | 0.391 | 0.035 | 82.97 |
| 10 | 0.312 | 0.027 | 93.73 |
| $IC_{50}$ | | | 0.105 |

TABLE 8

| 18-095 | Mean | SE | expression inhibition rate (%) |
|---|---|---|---|
| Control | 0.192 | 0.036 | 100.00 |
| 0 | 1.000 | 0 | 0.00 |
| 0.01 | 0.699 | 0.084 | 37.25 |
| 0.1 | 0.663 | 0.053 | 41.71 |
| 1 | 0.504 | 0.081 | 61.39 |
| 10 | 0.268 | 0.042 | 90.59 |
| $IC_{50}$ | | | 0.227 |

TABLE 9

| 18-177 | Mean | SE | expression inhibition rate (%) |
|---|---|---|---|
| Control | 0.267 | 0.037 | 100 |
| 0 | 1 | 0 | 0 |
| 0.01 | 0.96 | 0.166 | 5.46 |
| 0.1 | 0.839 | 0.077 | 21.96 |
| 1 | 0.742 | 0.129 | 35.20 |
| 10 | 0.438 | 0.084 | 76.67 |
| $IC_{50}$ | | | 1.310 |

TABLE 10

| 18-186 | Mean | SE | expression inhibition rate (%) |
|---|---|---|---|
| Control | 0.222 | 0.043 | 100.00 |
| 0 | 1.000 | 0 | 0.00 |
| 0.01 | 0.825 | 0.132 | 22.49 |
| 0.1 | 0.569 | 0.031 | 55.40 |
| 1 | 0.586 | 0.055 | 53.21 |
| 10 | 0.583 | 0.053 | 53.60 |
| $IC_{50}$ | | | 0.078 |

TABLE 11

| 18-273 | Mean | SE | expression inhibition rate (%) |
|---|---|---|---|
| Control | 0.283 | 0.06 | 100 |
| 0 | 1 | 0 | 0 |
| 0.01 | 0.408 | 0.033 | 82.57 |
| 0.1 | 0.835 | 0.092 | 23.01 |
| 1 | 0.832 | 0.072 | 23.43 |
| 10 | 0.46 | 0.045 | 75.31 |
| $IC_{50}$ | | | 1.776 |

TABLE 12

| 18-233 | Mean | SE | expression inhibition rate (%) |
|---|---|---|---|
| Control | 0.186 | 0.027 | 100.00 |
| 0 | 1.000 | 0 | 0.00 |
| 0.01 | 0.933 | 0.047 | 8.23 |
| 0.1 | 0.757 | 0.029 | 29.85 |
| 1 | 0.712 | 0.045 | 35.38 |
| 10 | 0.656 | 0.04 | 42.26 |
| $IC_{50}$ | | | 10.24 |

As can be understood from data of FIGS. 4 to 13, the compounds of the present invention inhibited the expression of the extracellular matrix, collagen I$\alpha$1 (Col1$\alpha$), in proximal tubular cells. In addition, in the proximal tubular cells, the compounds of the present invention generally inhibited the expression of the extracellular matrix, collagen I$\alpha$1 (Col1$\alpha$), in a concentration-dependent manner (except for the compound of Example 9). Also, the compound of Comparative Example decreased the expression level of the extracellular matrix, collagen I$\alpha$1 (Col1$\alpha$).

However, the compounds of the present invention were found to more effectively inhibit the expression of the extracellular matrix, collagen I$\alpha$1 (Col1$\alpha$), because their $IC_{50}$ values were at least three-fold lower than that of the compound of Comparative Example.

Found to suppress the tubulointestitual accumulation of collagen by inhibiting the expression of the extracellular matrix, collagen I$\alpha$1, in proximal tubular cells, the compounds of the present invention can therefor suppress renal fibrosis.

The invention claimed is:

1. A method for treating kidney disease in a subject in need thereof, comprising administering to the subject a composition in an amount sufficient for treatment of kidney disease, wherein the kidney disease is diabetic kidney disease, the composition comprising a compound selected from among the following compounds, or a pharmaceutically acceptable salt thereof:

1-(pyridin-2-yl)-3-phenyl-4-propyl-1H-pyrazol-5-ol;
1-(pyridin-2-yl)-3-phenyl-4-propyl-1H-pyrazol-5-ol-.HCl;
3-(3-methoxyphenyl)-1-(pyridin-2-yl)-1H-pyrazol-5(4H)-one;
3-(4-bromophenyl)-1-(pyridin-2-yl)-1H-pyrazol-5-ol;
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol;
3-(2-(benzo[d][1,3]dioxol-5-yl)phenyl)-1-(pyridin-2-yl)-1H-pyrazol-5-ol;
3-(biphenyl-4-yl)-1-(pyrimidin-2-yl)-1H-pyrazol-5-ol; and
3-{2-(4-hydroxy-3-methoxyphenyl)vinyl}-4-propyl-1-(2-pyridinyl)pyrazol-5-ol.

2. A method for treating kidney disease in a subject in need thereof, comprising administering to the subject a composition in an amount sufficient for treatment of kidney disease, wherein the kidney disease is diabetic kidney disease, the composition comprising a compound selected from among the following compounds, or a pharmaceutically acceptable salt thereof:

1-(pyridin-2-yl)-3-phenyl-4-propyl-1H-pyrazol-5-ol-.HCl;
3-(4-bromophenyl)-1-(pyridin-2-yl)-1H-pyrazol-5-yl acetate;
3-(3-iodophenyl)-1-(pyridin-2-yl)-1H-pyrazol-5-ol;
3-((naphthalen-3-yloxy)methyl)-1-(pyridin-2-yl)-1H-pyrazol-5-ol; and
3-(biphenyl-4-yl)-1-(pyrimidin-2-yl)-1H-pyrazol-5-ol.

3. The method of claim 1 wherein the subject is a mammal.

4. The method of claim 2 wherein the subject is a mammal.

* * * * *

SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: forward primer for Collagen I alpha 1 gene of
      mouse

<400> SEQUENCE: 1
cggatagcag attgagaaca tccg                                         24

<210> SEQ ID NO 2
<211> LENGTH: 21
<212> TYPE: DNA
<213> ORGANISM: Artificial Sequence
<220> FEATURE:
<223> OTHER INFORMATION: reverse primer for Collagen I alpha 1 gene of mouse

<400> SEQUENCE: 2
cggctgagta cggaacacac a                                              21

<210> SEQ ID NO 3
<211> LENGTH: 23
<212> TYPE: DNA
<213> ORGANISM: Artificial Sequence
<220> FEATURE:
<223> OTHER INFORMATION: forward primer for Collagen IV gene of mouse

<400> SEQUENCE: 3
cacgagcttc cctggtagtc gtg                                            23

<210> SEQ ID NO 4
<211> LENGTH: 20
<212> TYPE: DNA
<213> ORGANISM: Artificial Sequence
<220> FEATURE:
<223> OTHER INFORMATION: reverse primer for Collagen IV gene of mouse

<400> SEQUENCE: 4
ggacaacctt tgctgcctca                                                20

<210> SEQ ID NO 5
<211> LENGTH: 20
<212> TYPE: DNA
<213> ORGANISM: Artificial Sequence
<220> FEATURE:
<223> OTHER INFORMATION: forward primer for F4/80 gene of mouse

<400> SEQUENCE: 5
ctgtaaccgg atggcaaact                                                20

<210> SEQ ID NO 6
<211> LENGTH: 20
<212> TYPE: DNA
<213> ORGANISM: Artificial Sequence
<220> FEATURE:
<223> OTHER INFORMATION: reverse primer for F4/80 gene of mouse

<400> SEQUENCE: 6
atggccaagg caagacatac                                                20

<210> SEQ ID NO 7
<211> LENGTH: 22
<212> TYPE: DNA
<213> ORGANISM: Artificial Sequence
<220> FEATURE:
<223> OTHER INFORMATION: forward primer for fibronectin gene of mouse

<400> SEQUENCE: 7
cggcgtatgc tgtcactggc cg                                             22

<210> SEQ ID NO 8
<211> LENGTH: 20
<212> TYPE: DNA
<213> ORGANISM: Artificial Sequence
<220> FEATURE:
<223> OTHER INFORMATION: reverse primer for fibronectin gene of mouse

<400> SEQUENCE: 8
aagttgaagg cagccacctg                                                20

```
<210> SEQ ID NO 9
<211> LENGTH: 20
<212> TYPE: DNA
<213> ORGANISM: Artificial Sequence
<220> FEATURE:
<223> OTHER INFORMATION: forward primer for TGF-beta 1 gene of mouse

<400> SEQUENCE: 9
ggactctcca cctgcaagac                                              20

<210> SEQ ID NO 10
<211> LENGTH: 20
<212> TYPE: DNA
<213> ORGANISM: Artificial Sequence
<220> FEATURE:
<223> OTHER INFORMATION: reverse primer for TGF-beta 1 gene of mouse

<400> SEQUENCE: 10
gactggcgag ccttagtttg                                              20

<210> SEQ ID NO 11
<211> LENGTH: 20
<212> TYPE: DNA
<213> ORGANISM: Artificial Sequence
<220> FEATURE:
<223> OTHER INFORMATION: forward primer for 18S rRNA gene of mouse

<400> SEQUENCE: 11
cgaaagcatt tgccaagaat                                              20

<210> SEQ ID NO 12
<211> LENGTH: 20
<212> TYPE: DNA
<213> ORGANISM: Artificial Sequence
<220> FEATURE:
<223> OTHER INFORMATION: reverse primer 18S rRNA gene of mouse

<400> SEQUENCE: 12
agtcggcatc gtttatggtc                                              20

<210> SEQ ID NO 13
<211> LENGTH: 20
<212> TYPE: DNA
<213> ORGANISM: Artificial Sequence
<220> FEATURE:
<223> OTHER INFORMATION: forward primer for Collagen I alpha 1 gene of
      mouse

<400> SEQUENCE: 13
gaacatcacc taccactgca                                              20

<210> SEQ ID NO 14
<211> LENGTH: 20
<212> TYPE: DNA
<213> ORGANISM: Artificial Sequence
<220> FEATURE:
<223> OTHER INFORMATION: reverse primer for Collagen I alpha 1 gene of
      mouse

<400> SEQUENCE: 14
gttgggatgg agggagttta                                              20
```